(12) United States Patent
Pottie et al.

(10) Patent No.: US 10,219,990 B2
(45) Date of Patent: Mar. 5, 2019

(54) SOLUBILIZING AGENTS FOR UV FILTERS IN COSMETIC FORMULATIONS

(71) Applicant: BASF SE, Ludwigshafen (DE)

(72) Inventors: Laurence Pottie, Köln (DE); Ansgar Behler, Bottrop (DE); Stanislaw Krus, Lörrach (DE); Jochen Giesinger, Grenzach-Wyhlen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/534,054

(22) PCT Filed: Dec. 9, 2015

(86) PCT No.: PCT/EP2015/079084
§ 371 (c)(1),
(2) Date: Jun. 8, 2017

(87) PCT Pub. No.: WO2016/091930
PCT Pub. Date: Jun. 16, 2016

(65) Prior Publication Data
US 2017/0360666 A1 Dec. 21, 2017

(30) Foreign Application Priority Data
Dec. 9, 2014 (EP) .................................. 14196988

(51) Int. Cl.
*A61K 8/35* (2006.01)
*A61K 8/37* (2006.01)
*A61K 8/49* (2006.01)
*A61Q 17/04* (2006.01)

(52) U.S. Cl.
CPC .................. *A61K 8/35* (2013.01); *A61K 8/37* (2013.01); *A61K 8/4966* (2013.01); *A61Q 17/04* (2013.01)

(58) Field of Classification Search
None
See application file for complete search history.

(56) References Cited

U.S. PATENT DOCUMENTS

| | | |
|---|---|---|
| 5,338,539 A | 8/1994 | Raspanti |
| 5,489,431 A | 2/1996 | Ascione et al. |
| 5,518,713 A | 5/1996 | Raspanti |
| 5,601,811 A | 2/1997 | Gallagher et al. |
| 5,955,060 A | 9/1999 | Hüglin et al. |
| 5,985,925 A | 11/1999 | Josso et al. |
| 6,409,998 B1 | 6/2002 | Candau et al. |
| 6,440,401 B1 | 8/2002 | Heywang et al. |
| 2004/0247536 A1 | 12/2004 | Chaudhuri |
| 2014/0194646 A1 | 7/2014 | Allen et al. |
| 2016/0310381 A1 | 10/2016 | Behler et al. |
| 2017/0027831 A1 | 2/2017 | Dierker et al. |

FOREIGN PATENT DOCUMENTS

| | | |
|---|---|---|
| DE | 10138496 A1 | 2/2003 |
| DE | 10229995 A1 | 1/2004 |
| EP | 582189 A3 | 2/1994 |

(Continued)

OTHER PUBLICATIONS

International Preliminary Report on Patentability for Patent Application No. PCT/EP2015/079084, dated Jun. 13, 2017.
International Search Report for International Application No. PCT/EP2015/079084, dated date Feb. 3, 2016.
Written Opinion of the International Searching Authority for International Application No. PCT/EP2015/079084, dated Jun. 16, 2016.
"Cosmetic compositions against the damaging effect of sunlight", IP.com Journal, IP.com Inc., West Henrietta, NY, US, XP013129039, Jan. 2009.
Extended European Search Report for EP Application No. 14196988.1, dated Jun. 1, 2015.
Mintel, "baby shampoo", Database GNPD [Online], XP002739588, Oct. 2014, Database accession No. 2751401.

*Primary Examiner* — Aradhana Sasan
(74) *Attorney, Agent, or Firm* — Drinker Biddle & Reath LLP

(57) ABSTRACT

The present invention relates to the use of the compounds (A) corresponding to formula (1)

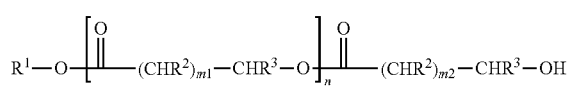

wherein
$R^1$ is hydrogen; a linear or branched $C_1$-$C_{30}$ aliphatic hydrocarbon residue comprising 0, 1, 2 or 3 double bonds;
$R^2$ independently from each other are hydrogen; methyl; ethyl; —OH; —COOR$^4$; —CH$_2$—OH; and —CH$_2$—COOR$^4$;
$R^4$ is hydrogen; or a linear or branched $C_1$-$C_{30}$ aliphatic hydrocarbon residue comprising 0, 1, 2 or 3 double bonds;
$R^3$ independently from each other are hydrogen; methyl; ethyl; —OH; —COOR$^5$; —CH$_2$—OH; and —CH$_2$—COOR$^5$;
$R^5$ is hydrogen; or a linear or branched $C_1$-$C_{30}$ aliphatic hydrocarbon residue comprising 0, 1, 2 or 3 double bonds;
n is at least 0.1 on average;
m1 and m2 independently from each other are 0; or 1;
with the proviso, that at least one of the radicals $R^1$, $R^4$ or $R^5$ represent a linear or branched $C_1$-$C_{30}$ aliphatic hydrocarbon residue comprising 0, 1, 2 or 3 double bonds,
as solubilizing agent for organic UV filters (B) selected from
(B1) benzophenone derivatives;
(B2) hydroxyphenyl triazine derivatives; and
(B3) trianilino-s-triazine derivatives.

22 Claims, No Drawings

(56) References Cited

FOREIGN PATENT DOCUMENTS

| | | |
|---|---|---|
| EP | 613893 A1 | 9/1994 |
| EP | 0709080 A1 | 5/1996 |
| EP | 775698 B1 | 5/1997 |
| EP | 1167358 A1 | 1/2002 |
| EP | 1093796 B1 | 2/2003 |
| EP | 0893119 B1 | 9/2003 |
| EP | 1371356 A3 | 12/2003 |
| EP | 1371357 A3 | 12/2003 |
| EP | 1371358 A3 | 12/2003 |
| FR | 2252840 A1 | 6/1975 |
| FR | 2816506 A1 | 5/2002 |
| GB | 1494915 A | 12/1977 |
| WO | WO-9700851 A1 | 1/1997 |
| WO | WO-0025731 A1 | 5/2000 |
| WO | WO-0185124 A1 | 11/2001 |
| WO | WO-0239974 A1 | 5/2002 |
| WO | WO-0341675 A3 | 5/2003 |
| WO | WO 2015/155095 A1 * | 10/2015 ............... A61K 8/49 |

* cited by examiner

SOLUBILIZING AGENTS FOR UV FILTERS IN COSMETIC FORMULATIONS

CROSS-REFERENCE TO RELATED APPLICATIONS

This application is a national stage application (under 35 U.S.C. § 371) of PCT/EP2015/079084, filed Dec. 9, 2015, which claims benefit of European Application No. 14196988.1, filed Dec. 9, 2014, both of which are incorporated herein by reference in their entirety.

The present invention relates to the use of specific oligohydroxy carboxylic acids as solubilizing agents for dissolving organic UV filters and the use of these compounds in cosmetically acceptable products for improved protection against UV radiation as well as cosmetic formulations exhibiting enhanced UV protection performance.

The present invention relates to improved formulations of oil-soluble crystalline organic UV absorbers.

It is well known that ultraviolet radiation (light) is harmful to human skin. Depending on the wavelength the UV radiation causes different types of skin damage. UV-B radiation (about 290 to about 320 nm) is responsible for sunburn and can cause skin cancer. UV-A radiation (about 320 to about 400 nm) while producing tanning of the skin, contributes also to sunburn and the induction of skin cancers. Moreover, the harmful effects of the UV-B radiation may be aggravated by UV-A radiation.

Therefore, an effective sunscreen formulation preferably comprises both at least one UV-A, UV-B filter and a broad band UV filter covering the full range of about 290 nm to about 400 nm to prevent the human skin from damaging by the sunlight.

Very effective organic UV filters are the classes of benzophenone derivatives, hydroxyphenyl triazine derivatives and trianilino-s-triazine derivatives.

Unfortunately, these UV absorber have a poor oil-solubility at a certain concentration and tend to crystallization. Consequently, the UV protection efficacy is significantly decreased.

Moreover, the oil soluble UV filters should be included in cosmetic sun care products, preferably emulsions, without any impact on the sensorial characteristic of the emulsion. For this reason, the optimal distribution of the UV absorber within the hydro-lipid film left on the skin after spreading should be guaranteed.

It is therefore an object of the present invention to find UV absorber formulations which have improved properties regarding the UV absorber.

Surprisingly it was found that certain oligohydroxy carboxylic acids guarantee optimal distribution of the organic UV absorber within the hydro-lipid film of the UV absorber formulation left on the skin after spreading and promotes the highest degree of solubilization of the organic UV absorber.

Therefore, the present invention relates to the use of the compounds (A) corresponding to formula

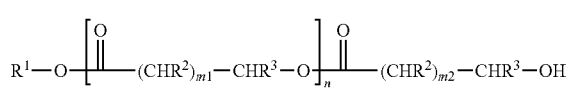

(1)

wherein
$R^1$ is hydrogen; a linear or branched $C_1$-$C_{30}$ aliphatic hydrocarbon residue comprising 0, 1, 2 or 3 double bonds;
$R^2$ independently from each other are hydrogen; methyl; ethyl; —OH; —COOR$^4$; —CH$_2$—OH; and —CH$_2$—COOR$^4$;
$R^4$ is hydrogen; or a linear or branched $C_1$-$C_{30}$ aliphatic hydrocarbon residue comprising 0, 1, 2 or 3 double bonds;
$R^3$ independently from each other are hydrogen; methyl; ethyl; —OH; —COOR$^5$; —CH$_2$—OH; and —CH$_2$—COOR$^5$;
$R^5$ is hydrogen; or a linear or branched $C_1$-$C_{30}$ aliphatic hydrocarbon residue comprising 0, 1, 2 or 3 double bonds;
n is at least 0.1 on average;
m1 and m2 independently from each other are 0; or 1;
with the proviso, that at least one of the radicals $R^1$, $R^4$ or $R^5$ represent a linear or branched $C_1$-$C_{30}$ aliphatic hydrocarbon residue comprising 0, 1, 2 or 3 double bonds,
as solubilizing agent for organic UV filters (B) selected from
(B1) benzophenone derivatives;
(B2) hydroxyphenyl triazine derivatives; and
(B3) trianilino-s-triazine derivatives.

The compounds of formula (1) may be present in form of mixtures or as single compounds. In the meaning of the present invention mixtures of the compound of formula (1) are suitable in general. The single components of these mixtures may for example differ with regard to the oligomerization degree. If hydroxy carboxylic acids are used for the preparation of the compounds of formula (1), which comprise more than one carboxylic group and/or more than one alcoholic OH-group, also structural isomerics resulting from the esterification reaction are suitable as single components for these mixtures. As a matter of course it is also possible to separate the reaction mixtures obtained according to the preparation process according to usual separating processes, for example by distillation or by chromatographic methods.

The average oligomerization degree for the compounds of formula (1) may be calculated by addition of the number 1 to the value of the variables n.

Suitable linear or branched aliphatic $C_1$-$C_{30}$ hydrocarbon radicals and 0, 1, 2 or 3 double bonds are the corresponding $C_1$-$C_{30}$alkyl radicals, $C_2$-$C_{30}$alkenyl radicals, $C_3$-$C_{30}$alkadienyl radicals and $C_4$-$C_{30}$alkatrienyl radicals.

Preferably at least one of the radicals $R^1$, $R^4$ or $R^5$ is a linear or branched aliphatic $C_6$-$C_{30}$ hydrocarbon radical and 0, 1, 2 or 3 double bonds. Preferably $R^1$, $R^4$ and $R^5$ independently from each other are selected from methyl, ethyl, propyl, isopropyl, n-butyl, 2-butyl, sec.-butyl, tert.-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, arachinyl, behenyl, lignocerinyl, melissinyl, isotridecyl, isostearyl, oleyl, linoleyl, linolenyl, etc.

More preferably, at least one of the radicals $R^1$, $R^4$ and $R^5$ is methyl; ethyl; n-propyl; isopropyl; n-butyl; isobutyl; sec.-butyl; tert.-butyl; n-pentyl; isoamyl; n-hexyl; 2-ethylhexyl; n-heptyl; n-octyl; n-nonyl; n-decyl; 2-propylheptyl; n-undecyl; n-dodecyl; n-tridecyl; n-tetradecyl; n-pentadecyl; n-hexadecyl; n-heptadecyl; n-octadecyl; n-nonadecyl; arachinyl; behenyl; lingocerinyl; melissinyl; isotridecyl; isostearyl; oleyl; linoleyl; linolenyl or a combination of at least two of these radicals.

Preferably, at least one of the radicals $R^1$, $R^4$ or $R^5$ is a linear or branched aliphatic $C_6$-$C_{30}$ hydrocarbon radical and 0, 1, 2 or 3 double bonds. Most preferably $R^1$, $R^4$ and $R^5$ independently from each other are selected from n-hexyl, 2-ethylhexyl, n-heptyl, n-octyl, n-nonyl, n-decyl, n-undecyl, n-dodecyl, n-tridecyl, n-Tetradecyl, n-pentadecyl, n-hexadecyl, n-heptadecyl, n-octadecyl, n-nonadecyl, arachinyl, behenyl, lignocerinyl, melissinyl, isotridecyl, isostearyl, oleyl, linoleyl, linolenyl, and combinations thereof.

The radicals $R^1$, $R^4$ and $R^5$ may be derived from pure alcohols or mixtures of alcohols. Preferably, large-scale available alcohols or alcohol mixtures are used. Preferably, $R^1$, $R^4$ and $R^5$ in this case independently from each other are selected from predominantly linear alkyl-, alkenyl-, alkadienyl- and alkatrienyl radicals according to their frequency in natural or synthetic fatty acids and the corresponding fatty alcohols.

In a further embodiment of the present invention $R^1$, $R^4$ and $R^5$ independently from each other are derived from fatty alcohols, which are based on technical alcohol mixtures like the alcohol mixtures resulting from the hydration of technical methyl esters on the base of fats and oils including alcohol mixtures accumulating at the hydration of aldehydes from the oxo synthesis or alcohol mixtures accumulating from the dimerization of unsaturated fatty alcohols.

Preferably, one of the radicals $R^1$, $R^4$ and $R^5$ is derived from saturated linear $C_8$-$C_{18}$ hydro carbons.

Most preferably, at least one of the radicals $R^1$, $R^4$ and $R^5$ is derived from a mixture of linear saturated $C_{12}$-$C_{14}$-alkohols.

Furthermore, at least one of the radicals $R^1$, $R^4$ and $R^5$ is derived from a $C_{16}$-/$C_{18}$fatty alcohol mixture. Mixtures from cetyl (hexadecyl) and stearyl (octadecyl) are called cetearyl.

Preferably, m1 and m2 have the same meaning.

The compounds of formula (1) represent ester of oligohydroxy carboxylic acids. These compounds can be derived from commercial hydroxy carboxylic acids like lactic acid, glycolic acid, malic acid, tartaric acid, tartronic acid and mixtures thereof.

Preferably in the meaning of the present invention oligohydroxy carboxylic acids of formula

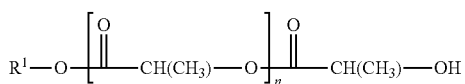

(2)

are used, wherein
$R^1$ is hydrogen; or a linear or branched $C_1$-$C_{30}$ aliphatic hydrocarbon residue comprising 0, 1, 2 or 3 double bonds; and
n is at least 0.1 on average.

Preferably, the compounds of formula (1) and (2) are derived from lactic acid, glycolic acid, malic acid, tartaric acid or mixtures thereof.

In the compounds of formula (1) n is preferably a number from 0.1 to 100, most preferably from 0.15 bis 50, especially from 0.2 to 20.

The compounds of formula (1) are preferably prepared by an esterification reaction wherein the esterification is carried out in the presence of an alcohol $R^1$—OH, wherein $R^1$ is hydrogen; or a linear or branched aliphatic $C_1$-$C_{30}$ hydrocarbon and 0, 1, 2 or 3 double bonds,
or the esterification product of the hydroxycarboxylic acid is reacted with at least one alcohol $R^1$—OH.

The oligohydroxy carboxylic acids in the meaning of the present invention are preferably used for solubilizing organic UV filters (=component (B)), especially crystalline, oil-soluble UV filters.

Preferred benzophenone derivatives (B1) correspond to the formula

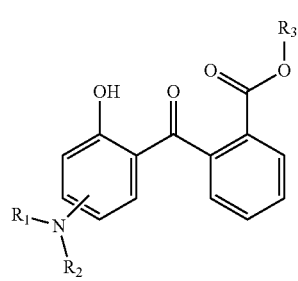

(BPH-01)

wherein
$R_1$ and $R_2$ independently from each other are hydrogen; $C_1$-$C_{20}$alkyl; $C_3$-$C_{10}$cycloalkyl; or $C_3$-$C_{11}$cycloalkenyl, wherein the radicals $R_1$ and $R_2$ together with the nitrogen atom, to which they are bonded may form a 5- or 6-membered ring; and
$R_3$ is $C_1$-$C_{20}$alkyl.

Most preferred benzophenone derivatives (B1) according to the present invention correspond to the formula

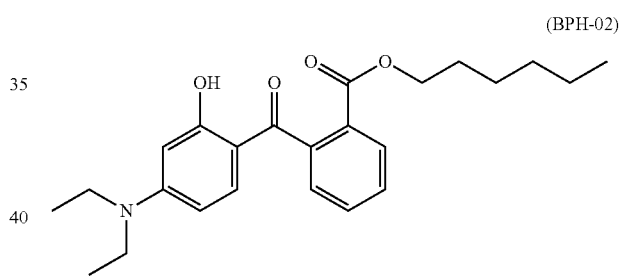

(BPH-02)

Preferred hydroxyphenyl triazine derivatives (B2) according to the present invention correspond to formula

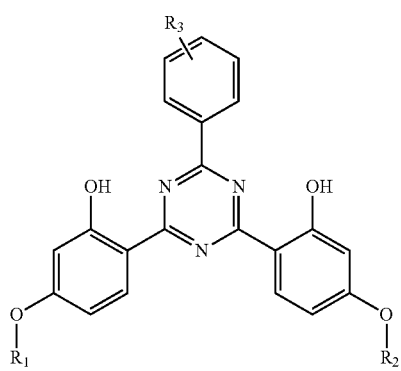

(HTP-01)

wherein
$R_1$ and $R_2$ independently from each other are $C_1$-$C_{18}$alkyl; and
$R_3$ is $C_1$-$C_{10}$alkoxy.

Most preferred hydroxyphenyl triazine derivatives (B2) according to the present invention correspond to formula

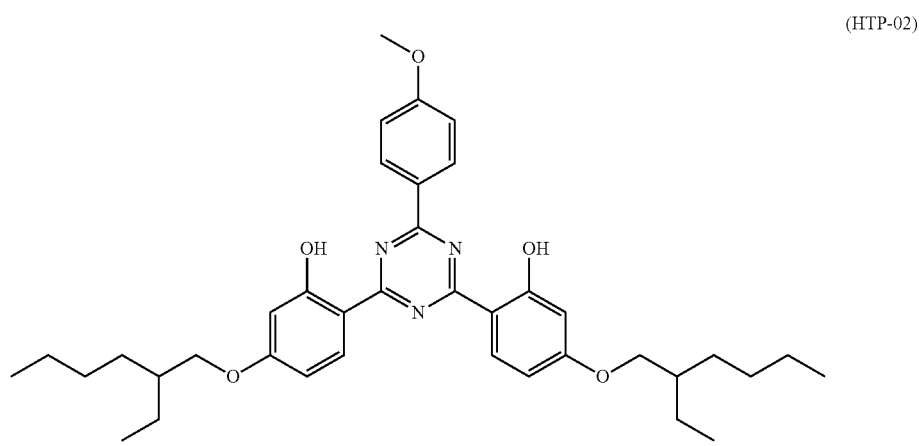 [SMILES: CCCCC(CC)COc1ccc(-c2nc(-c3ccc(OC)cc3)nc(-c3ccc(OCC(CC)CCCC)cc3O)n2)c(O)c1]

(HTP-02)

Further preferred hydroxyphenyl triazine derivatives (B2) according to the present invention correspond to formula

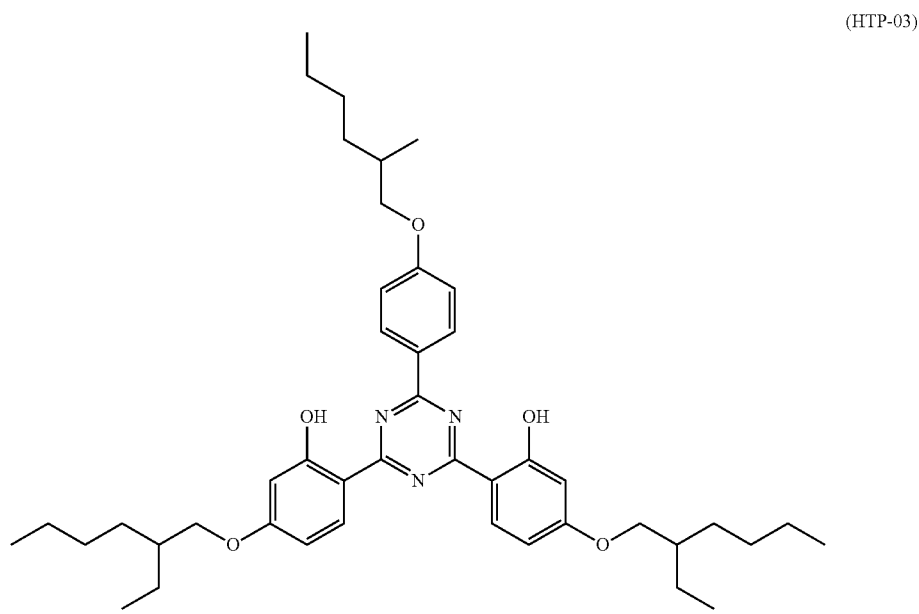 [SMILES: CCCCC(C)COc1ccc(-c2nc(-c3ccc(OCC(CC)CCCC)cc3O)nc(-c3ccc(OCC(CC)CCCC)cc3O)n2)cc1]

(HTP-03)

The hydroxyphenyl triazine derivatives (B2) as used in the present invention can be prepared by manners known per se, as described for example in EP 775698 B1.

Preferred trianilino-s=triazine derivatives (B3) correspond to the formula

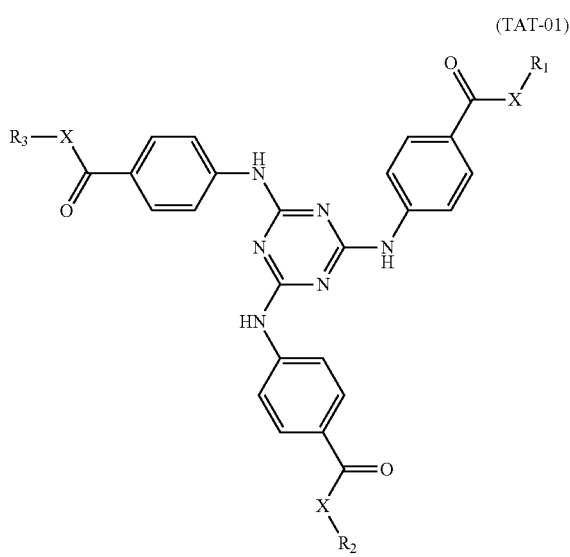

(TAT-01)

wherein
R$_1$, R$_2$ and R$_3$ independently from each other are optionally substituted C$_1$-C$_{20}$alkyl, C$_6$-C$_{10}$aryl or C$_6$-C$_{10}$eteroaryl;
X is O; or NR$_4$; and
R$_4$ is hydrogen; or optionally substituted C$_1$-C$_{20}$alkyl, aryl or heteroaryl.

Most preferred trianilino-s-triazine derivatives (B3) correspond to the formula

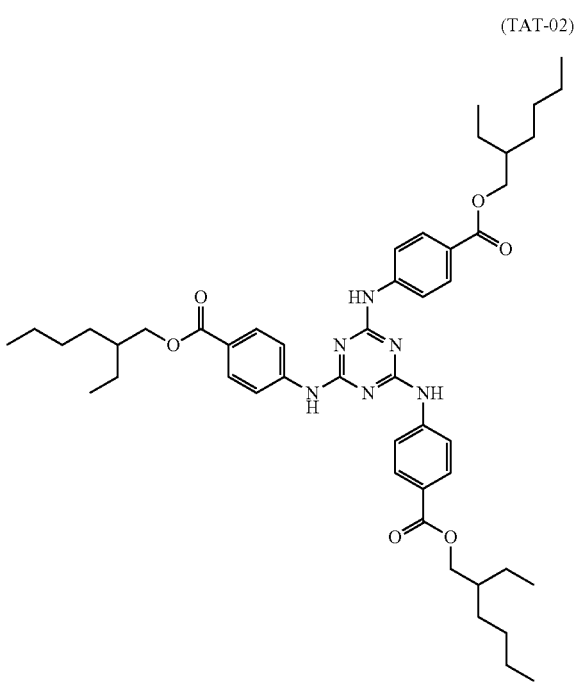 [SMILES: CCCCC(CC)COC(=O)c1ccc(Nc2nc(Nc3ccc(C(=O)OCC(CC)CCCC)cc3)nc(Nc3ccc(C(=O)OCC(CC)CCCC)cc3)n2)cc1]

(TAT-02)

Preferably the organic UV filters (B) according to the present invention are used as mixtures,
Preferably mixtures of UV filters (BPH-02), (HTP-02) and (TAT-02) are used,
Further preferred mixtures of organic UV filters according to the present invention are:

UV filters (BPH-02) and (HTP-02);
UV filters (BPH-02) and (TAT-02); and
UV filters (HTP-02) and (TAT-02)
Preferably, the compound of formula

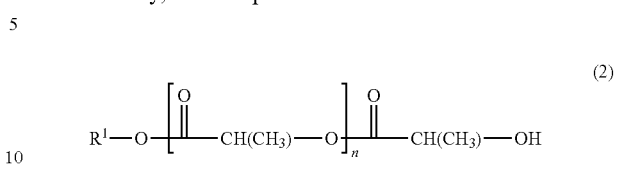

(2)

wherein
R$^1$ is hydrogen; or a linear or branched C$_1$-C$_{30}$ aliphatic hydrocarbon residue comprising 0, 1, 2 or 3 double bonds; and
n is at least 0.1 on average;
is used as solubilizing agent (A) for the UV filters (B) selected from (BPH-02), (HTP-02) and (TAT-02).

Furthermore, the present invention relates to a cosmetic composition, which preferably comprises
(A) the compound of formula $$R^1-O\left[\overset{O}{\underset{\|}{C}}-(CHR^2)_{m1}-CHR^3-O\right]_n\overset{O}{\underset{\|}{C}}-(CHR^2)_{m2}-CHR^3-OH$$

(1)

wherein
R$^1$ is hydrogen; a linear or branched C$_1$-C$_{30}$ aliphatic hydrocarbon residue comprising 0, 1, 2 or 3 double bonds;
R$^2$ independently from each other are hydrogen; methyl; ethyl, —OH; —COOR$^4$; —CH$_2$—OH; and —CH$_2$—COOR$^4$;
R$^4$ is hydrogen; or a linear or branched C$_1$-C$_{30}$ aliphatic hydrocarbon residue comprising 0, 1, 2 or 3 double bonds;
R$^3$ independently from each other are hydrogen; methyl; ethyl; —OH; —COOR$^5$; —CH$_2$—OH; and —CH$_2$—COOR$^5$;
R$^5$ is hydrogen; or a linear or branched C$_1$-C$_{30}$ aliphatic hydrocarbon residue comprising 0, 1, 2 or 3 double bonds;
n is at least 0.1;
m1 and m2 independently from each other are 0; or 1;
with the proviso, that at least one of the radicals R$^1$, R$^4$ or R$^5$ are a linear or branched C$_1$-C$_{30}$ aliphatic hydrocarbon residue comprising 0, 1, 2 or 3 double bonds; and
(B) organic UV filters selected from
(B1) benzophenone derivatives,
(B2) hydroxyphenyl triazine derivatives; and
(B3) trianilino-s-triazine derivatives.

Preferably, the solubilizing agent (A) in the cosmetic composition according to the present invention corresponds to formula

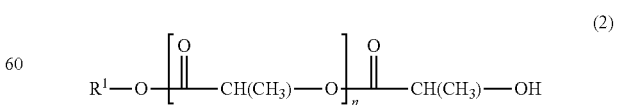

(2)

wherein
R$^1$ is hydrogen; or a linear or branched C$_1$-C$_{30}$ aliphatic hydrocarbon residue comprising 0, 1, 2 or 3 double bonds; and
n is at least 0.1 on average.

The cosmetic composition of the present invention preferably comprises
0.1 to 25% b.w. of a solubilizing agent (A);
0.1 to 20% b.w. of at least one organic UV filter (B); and
10 to 90% b.w. of a cosmetically acceptable carrier (C),
based on the total weight of the cosmetic end-product composition.

Preferably the cosmetic composition comprises
(A) a solubilizing agent of formula (2); and
(B) organic UV filters selected from (HTP-02), (BPH-02) and (TAT-02), Preferred are also cosmetic compositions, comprising
(A) a solubilizing agent of formula (2) and (B) mixtures of UV filters (HTP-02), (BPH-02) and (TAT-02).
(A) a solubilizing agent of formula (2) and (B) mixtures of UV filters (BPH-02) and (HTP-02).
(A) a solubilizing agent of formula (2) and (B) mixtures of UV filters (HTP-02) and (TAT-02).
(A) a solubilizing agent of formula (2) and (B) mixtures of UV filters (BPH-02) and (TAT-02).

Preferably the compound of formula

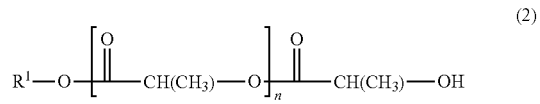

(2)

wherein
$R^1$ is hydrogen; or a linear or branched $C_1$-$C_{30}$ aliphatic hydrocarbon residue comprising 0, 1, 2 or 3 double bonds; and
n is at least 0.1 on average;
is used as solubilizing agent (A) for the UV filters (B) selected from (BPH-02) as claimed in claim 10, (HTP-02) as claimed in claim 12 and (TAT-02) as claimed in claim 15.

The cosmetic composition according to the present invention may comprise one or more than one additional UV absorbers (component (D)) as described in the Tables 1 and 2.

TABLE 1

Suitable UV filter substances which can be additionally used with the organic UV absorbers (B) according to the present invention p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative;
diphenylacrylates, for example 2-ethylhexyl 2-cyano-3,3-diphenylacrylate, and 3-(benzofuranyl) 2-cyanoacrylate;
3-imidazol-4-ylacrylic acid and esters;
benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;
polymeric UV absorbers, for example the benzylidene malonate derivatives described in EP-A-709 080;
cinnamic acid derivatives, for example the 4-methoxycinnamic acid 2-ethylhexyl ester and isoamyl ester or cinnamic acid derivatives described in U.S. Pat. No. 5,601,811 and WO 97/00851;
camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylene-dimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
phenyl-benzimidazole derivatives as disclosed in EP 1 167 358

TABLE 2

Suitable UV filter substances and adjuvants which can be additionally used with the UV absorbers (B) according to the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | 1-[4-(1,1-dimethylethyl)phenyl]-3-(4-methoxyphenyl)propane-1,3-dione; Avobenzone | 70356-09-1 |
| 12 | Methyl N,N,N-trimethyl-4-[(4,7,7-trimethyl-3-oxobicyclo[2,2,1]hept-2-ylidene)methyl]anilinium sulphate; Mexoryl SO | 52793-97-2 |
| 22 | 3,3,5-Trimethyl cyclohexyl-2-hydroxy benzoate; homosalate | 118-56-9 |
| 23 | Isopentyl p-methoxycinnamate; isoamyl methoxy cinnamate | 71617-10-2 |
| 27 | Menthyl-o-aminobenzoate | 134-09-8 |

TABLE 2-continued

Suitable UV filter substances and adjuvants which can be additionally used with the UV absorbers (B) according to the present invention

| No. | Chemical Name | CAS No. |
|---|---|---|
| 28 | Menthyl salicylate | 89-46-3 |
| 29 | 2-Ethylhexyl 2-cyano,3,3-diphenylacrylate; Octocrylene | 6197-30-4 |
| 31 | 2-ethylhexyl 4-methoxycinnamate; Octyl Methoxy Cinnamate | 5466-77-3 |
| 32 | 2-ethylhexyl salicylate | 118-60-5 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethyl-butyl)-phenol]; Tinosorb M | 103597-45-1 |
| 46 | 1H-Benzimidazole-4,6-disulfonic acid, 2,2'-(1,4-phenylene)bis-, disodium salt | 180898-37-7 |
| 47 | Benzoic acid, 4,4'-[[6-[[4-[[(1,1-dimethylethyl)amino]carbonyl]phenyl]amino]1,3,5-triazine-2,4-diyl]diimino]bis-, bis(2-ethylhexyl)ester; diethylhexyl butamido triazone; Uvasorb HEB | 1154702-15-5 |
| 48 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 1155633-54-8 |
| 49 | Dimethicodiethylbenzalmalonate; Polysilicone 15; Parsol SLX | 207574-74-1 |
| 50 | Benzenesulfonic acid, 3-(2H-benzotriazol-2-yl)-4-hydroxy-5-(1-methylpropyl)-, monosodium salt; Tinogard HS | 92484-48-5 |
| 52 | 1-Dodecanaminium, N-[3-[[4-(dimethylamino)benzoyl]amino]propyl]-N,N-dimethyl-, salt with 4-methylbenzenesulfonic acid (1:1); Escalol HP610 | 156679-41-3 |
| 53 | 1-Propanaminium, N,N,N-trimethyl-3-[(1-oxo-3-phenyl-2-propenyl)-amino]-, chloride | 177190-98-6 |
| 54 | 1H-Benzimidazole-4,6-disulfonic acid, 2,2'-(1,4-phenylene)bis- | 1170864-82-1 |
| 57 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 58 | 2-Propenoic acid, 3-(1H-imidazol-4-yl)- | 104-98-3 |
| 59 | Benzoic acid, 2-hydroxy-, [4-(1-methylethyl)phenyl]methyl ester | 94134-93-7 |
| 60 | 1,2,3-Propanetriol, 1-(4-aminobenzoate); glyceryl PABA | 136-44-7 |
| 61 | Benzeneacetic acid, 3,4-dimethoxy-a-oxo- | 4732-70-1 |
| 62 | 2-Propenoic acid, 2-cyano-3,3-diphenyl-, ethyl ester | 5232-99-5 |
| 63 | Anthralinic acid, p-menth-3-yl ester | 134-09-8 |
| 64 | 2,2'-bis(1,4-phenylene)-1H-benzimidazole-4,6-disulphonic acid mono sodium salt or Disodium phenyl dibenzimidazole tetrasulfonate or Neo Heliopan AP | 349580-12-7, |
| 68 | sterols (cholesterol, lanosterol, phytosterols), as described in WO0341675 | |
| 69 | mycosporines and/or mycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes,) | |
| 70 | alpha-lipoic-acid as described in DE 10229995 | |
| 71 | synthetic organic polymers as described in EP 1371358, [0033]-[0041] | |
| 72 | phyllosilicates as described in EP 1371357 [0034]-[0037] | |
| 73 | silica compounds as described in EP1371356, [0033]-[0041] | |
| 74 | inorganic particles as described in DE10138496 [0043]-[0055] | |
| 75 | latex particles as described in DE10138496 [0027]-[0040] | |
| 76 | 1H-Benzimidazole-4,6-disulfonic acid, 2,2'-(1,4-phenylene)bis-, disodium salt; Bisimidazylate; Neo Heliopan APC | 180898-37-7 |
| 81 | 2,4,6-Tris(p-biphenylyl)-s-triazine, Tinosorb A2B | 31274-51-8 |
| 82 | 2,4,6-Tris-1,1',4',1''-terphenyl-4-yl-1,3,5-triazine | |
| 83 | Di-2-ethylhexyl-3,5-dimethoxy-4-hydroxy-benzalmalonate (Oxynex ST, EMD Chemicals, as described in US 20040247536) | |

The cosmetic composition according to the present invention can be prepared by physically mixing the UV filter(s) (B) with the adjuvant using customary methods, for example by simply stirring together the individual components, especially by making use of the dissolution properties of already known cosmetic UV filters, like octyl methoxy cinnamate, salicylic acid isooctyl ester, etc. The UV filter (B) can be used, for example, without further treatment, or in the micronized state, or in the form of a powder.

The cosmetic or pharmaceutical compositions/preparations according to the invention may also contain one or one more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of $C_{12}$-$C_{15}$ alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctyl-stearate, iso-nonylstearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucylerucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Natural or Synthetic Triglycerides Including Glyceryl Esters and Derivatives

Di- or tri-glycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carboxylic acids and their salts: alkaline soap of sodium, potassium and ammonium, metallic soap of calcium or magnesium, organic basis soap such as Lauric, palmitic, stearic and oleic acid etc. . . . . Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycolether such as laureth-n, ceteareth-n, steareth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, C8-C22 alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, amonium and ethanolamine lauryl sulfates, lauyl ether sulfates, sodium laureth sulfates, sulfosuccinates, aceyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quaternary ammonium such as cetyltrimethylbroide amonium broide (CTBA), stearylalkonium. Amide derivatives, alkanolamides such as acylamide DEA, ethoxylated amides such as PEG-n acylamide, oxydeamide; polysiloxane/-polyalkyl/polyether copolymers and derivatives, dimethicone, copolyols, silicone polyethylene oxide copolymer, silicone glycol copolymer; propoxylated or POE-n ethers (Meroxapols); polaxamers or poly(oxyethylene)m-block-poly(oxypropylene)n-block(oxyethylene); zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethylammonium glycinates, cocoacylaminopropyldimethylammonium glycinate and 2-alkyl-3-carboxymethyl-3-hydroxyethyl-imidazolines each having from 8 to 18 carbon atoms in the alkyl or acyl group and also cocoacylaminoethylhydroxyethylcarboxymethylglycinate, N-alkylbetaine, N-alkylaminobetaines. alkylimidazolines, alkylopeptides, lipoaminoacides, self emulsifying bases and the compounds as described in K. F. DePolo, A short textbook of cosmetology, Chapter 8, Table 8-7, p 250-251.

Non ionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20[Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Adjuvants and Additives

The cosmetic/pharmaceutical preparations, for example creams, gels, lotions, alcoholic and aqueous/alcoholic solutions, emulsions, wax/fat compositions, stick preparations, powders or ointments, may in addition contain, as further adjuvants and additives, mild surfactants, su-per-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants, bacteria-inhibiting agents and the like.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicon dioxide, magnesium silicates, aluminium silicates, polysaccharides or derivatives thereof for example hyaluronic acid, xanthan gum, guar-guar, agar-agar, alginates, carraghenan, gellan, pectines, or modified cellulose such as hydroxycellulose, hydroxypropyl-methylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80 (steareth-10 allyl ether/acrylates copolymer), Salcare SC81 (acrylates copolymer), Salcare SC91 and Salcare AST (sodium acrylates copolymer/PPG-1 trideceth-6), sepigel 305 (polyacrylamide/laureth-7), Simulgel NS and Simulgel EG (hydroxyethyl acrylate/sodium acryloyldimethyl taurate copolymer), Stabilen 30 (acrylates/vinyl isodecanoate crosspolymer), Pemulen TR-1 (acrylates/C10-30 alkyl acrylate crosspolymer), Luvigel EM (sodium acrylates copolymer), Aculyn 28 (acrylates/-beheneth-25 methacrylate copolymer), etc.

Polymers

Suitable cationic polymers are, for example, cationic cellulose derivatives, for example a quaternised hydroxymethyl cellulose obtainable under the name Polymer JR 400 from Amerchol, cationic starches, copolymers of diallylammonium salts and acrylamides, quarternised vinyl-pyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat® L/Grünau), quaternised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chemviron), polyaminopolyamides, as described, for example, in FR-A-2 252 840, and the crosslinked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quaternised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylatetert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatized cellulose ethers and silicones. Furthermore the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients there come into consideration, for example, antiperspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl\times 2.5H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Hen-kel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2, 4-dichlorophenoxy)-phenol (Triclosan, Irgasan, Ciba Specialty Chemicals Inc.) has also proved especially effective.

Anti-Dandruff Agents

As anti-dandruff agents there may be used, for example, climbazole, octopirox and zinc pyri-thione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Antioxidants

In addition to the primary light-protective substances it is also possible to use secondary light-protective substances of the antioxidant kind that interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodi-propionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, hepta-thionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers) of sugars, nucleotides, nucleosides, peptides and lipids) of those mentioned active ingredients. HALS (="Hindered Amine Light Stabilizers") compounds may also be mentioned.

Further synthetic and natural antioxidants are listed e.g. in patent WO 0025731: Structures 1-3 (page 2), structure 4 (page 6), structures 5-6 (page 7) and compounds 7-33 (page 8-14).

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria Inhibiting Agents

Suitable preservatives include, for example, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo—A short textbook of cosmetology, Chapter 7, Table 7-2, 7-3, 7-4 and 7-5, p 210-219.

Typical examples of bacteria-inhibiting agents are preservatives that have a specific action against gram-positive bacteria, such as 2,4,4'-trichloro-2'-hydroxydroxydiphenyl ether, chlorhexidine (1,6-di(4-chlorophenyl-biguanido) hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethyiphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, *galbanum* oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romillat, irotyl and floramat alone or in admixture with one another.

Colourants

There may be used as colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Other Adjuvants

It is furthermore possible for the cosmetic preparations to contain, as adjuvants, anti-foams, such as silicones, structurants, such as maleic acid, solubilisers, such as ethylene glycol, propylene glycol, glycerol or diethylene glycol, opacifiers, such as latex, styrene/PVP or styrene/acrylamide copolymers, complexing agents, such as EDTA, NTA, alaninediacetic acid or phosphonic acids, propellants, such as propane/butane mixtures, $N_2O$, dimethyl ether, $CO_2$, $N_2$ or air, so-called coupler and developer components as oxidation dye precursors, reducing agents, such as thioglycolic acid and derivatives thereof, thiolactic acid, cysteamine, thiomalic acid or mercaptoethanesulfonic acid, or oxidising agents, such as hydrogen peroxide, potassium bromate or sodium bromate.

Suitable insect repellents are, for example, N,N-diethyl-m-toluamide, 1,2-pentanediol or insect repellent 3535; suitable self-tanning agents are, for example, dihydroxyacetone and/or erythrulose or dihydroxy acetone and/or dihydroxy acetone precursors as described in WO 01/85124 and/or erythrulose.

Polymeric Beads or Hollow Spheres as SPF Enhancers

The combination of the UV-absorbers and UV-absorber combinations, listed above, with SPF enhancers, such as non-active ingredients like Styrene/acrylates copolymer, silica beads, spheroidal magnesium silicate, crosslinked Polymethylmethacrylates (PMMA; Micopearl M305 Seppic), can maximize better the UV protection of the sun products. Holosphere additives (Sunspheres® ISP, Silica Shells Kobo.) deflect radiation and the effective path length of the photon is therefore increased (EP0893119). Some beads, as mentioned previously, pro-vide a soft feel during spreading. Moreover, the optical activity of such beads, e.g. Micropearl M305, cans modulate skin shine by eliminating reflection phenomena and indirectly may scatter the UV light.

Cosmetic or Pharmaceutical Preparations

Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eye shadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, parfume), parfume oils or parfume creams;

cosmetic hair-treatment preparations, e.g. hair-washing preparations in the form of shampoos and conditioners, hair-care preparations, e.g. pre-treatments preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:

in the form of liquid preparations as a W/O, O/W, O/W/O, W/O/WV or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellant gas or pump-action spray) or an aerosol, in the form of a foam, or in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milks and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pre-treatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

a$_1$) spontaneously emulsifying stock formulation, consisting of the UV absorber according to the invention, PEG-6-C$_{10}$oxoalcohol and sorbitan sesquioleate, to which water and any desired quaternary ammonium compound, for example 4% minkamidopropyl dimethyl-2-hydroxyethyl-ammonium chloride or Quaternium 80 is added;

a$_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl dimethyl-2-hydroxyethyl-ammonium chloride or Quaternium 80 is added;

b) quat-doped solutions of the UV absorber according to the invention in butyl triglycol and tributyl citrate;

c) mixtures or solutions of the UV absorber according to the invention with n-alkylpyrrolidone.

The cosmetic preparation according to the invention is characterized by excellent protection of human skin against the damaging effect of sunlight.

A. Solubility Tests

EXPERIMENTAL 2 ml of the solubilizing agent are filled into a 20 ml vial with cap. Afterwards 0.02 g (1%) of the respective substance (UV Filter) are weighed and added to the solvent. The vial is placed into a thermostat-controlled water bath, wherein the suspension/solution is stirred during seven days at 25° C.

If the substance added to the solubilizing agent is fully soluble, additional substance is added until precipitation can be observed.

After seven days, the sample is centrifuged for 30 minutes at 13000 rpm at 25° C. The supernatant is transferred into a small beaker. In case the sample is still turbid, it is filtered through a 0.2 μm non-steril Membrex 25 PET filter. Clear solutions must not be filtered. When a clear solution is obtained, the concentration of the substance is determined with UV/Vis-spectrometry. For this purpose, the sample may be diluted with a suitable solvent or, in case of lower concentrations, may be measured as it s.

The concentration of the UV-spectroscopic results is measured with the extinction coefficient, which is determined independently with a solvent of similar polarity like that one used for dilution of the saturated solutions.

The solubility can be calculated using the Lambert-Beer-Law equation.

Test Results:

TABLE

Solubility [%] of UV filters in solubilizing agents according to the present invention

| solubilizing agent (A) according to the present invention | UV filter compound of formula | | |
|---|---|---|---|
| | (HTP-02) | (TAT-02) | (BPH-02) |
| (Ethyl lactate) | 0.5 | 13.6 | 38.0 |
| (C8/10-monolactate) | 0.7 | 28.0 | 14.4 |
| C8/10-dilactate | 0.9 | 23.3 | 13.9 |
| C8/10-trilactate | 0.8 | 12.4 | 13.7 |
| C12/14-trilactate | 0.7 | 12.4 | 12.5 |
| C12/14-dilactate | 0.9 | 23.3 | 14.2 |
| (Iso-C18-monolactate) | 3.3 | 13.4 | 12.2 |
| (C 23-Guerbet-monolactate) | 2.9 | 11.9 | 11.2 |
| Benchmark 1: | | | |
| Spectrasolv DMDA (use limited to 2%) bad smell (Alkylamide) | 40% | 23% | >40% |

B. Formulation Examples

| | Trade name | INCI | B-1 | B-2 |
|---|---|---|---|---|
| A | Cetiol B | Dibutyl Adipate | 4.00 | 10.00 |
| | Oligolactate | C12-/14 Di-Lactate | 5.00 | 12.50 |
| | Tegosoft XC | Phenoxyethyl Caprylate | 4.00 | 10.00 |
| | Finnsolv EB | Ethylhexyl Benzoate | 4.00 | 10.00 |
| | Protectol PE | Phenoxyethanol | 1.00 | 2.50 |
| | compound (HTP-02) | Bis-Ethylhexyloxyphenol Methoxyphenyl Triazine | 2.00 | 5.00 |
| | compound (BPH-02) | Diethylamino Hydroxy-benzoyl Hexyl Benzoate | 4.50 | 11.25 |
| | compound (TAT-02) | Ethylhexyl Triazone | 3.00 | 7.50 |
| B | Water | Aqua | 62.20 | 155.50 |
| | Glycerin | Glycerin | 2.00 | 5.00 |
| | Pemulen TR-2 Polymer | Acrylates/C10-30 Alkyl Acrylate Crosspoyper | 0.20 | 0.50 |
| | Avicel PC611 | Microcrystalline Cellulose | 0.50 | 1.25 |
| C | Water | Aqua | 4.00 | 10.00 |
| | Eusolex 232 | PBSA | 2.00 | 5.00 |
| | Tris Amino Ultra Pur | Tromethamine | 1.60 | 4.00 |
| | Summary | | 100.00 | 250.00 |
| | Oil Phase | | 27.50 | |

| UV Filter | | in form | calculated |
|---|---|---|---|
| Solubility (%) | (BPH-02) | 4.50 | 5.4 |
| | (HTP-02) | 2.0 | 1.9 |
| | (TAT-02) | 3.0 | 2.5 |
| Calc. SPF-UVA/UVB-UVA-PF-Ratio | | 32.4-0.72-11.9 (SPF30)-2.51 | |
| SPF in vitro (Plate - application rate) | | 24.3 | |

Manufacturing instruction:
Heat part A and B to 80° C.
Add part A into B, homogenize
Add part C under turrax, cool to room temperature under stirring

Example B-3: Clear Sun Oil-Ethanol Spray SPF 30

| Phase | Ingredients | INCI | % by weight |
|---|---|---|---|
| A | Cetiol ® AB | C12-15 Alkyl Benzoate | 22.30 |
|   |  | Alkyl Oligolactate | 10.00 |
|   | Cetiol ® CC | Dicaprylyl Carbonate | 10.00 |
|   | Cosmedia ® DC | Hydrogenated Dimer Dilinoleyl/-Dimethylcarbonate Copolymer | 2.00 |
|   | Uvinul ® MC 80 | Ethylhexyl Methoxycinnamate | 10.00 |
|   | Uvinul ® A Plus | Diethylamino Hydroxybenzoyl Hexyl Benzoate | 7.00 |
|   | Neo Heliopan OS | Ethylhexyl Salicylate | 5.00 |
|   | Tinosorb ® S | Bis-Ethylhexyloxyphenol Methoxyphenyl Triazine | 2.50 |
| B | Cetiol ® C 5 | Coco-Caprylate | 16.00 |
| C | Vitamin E-Acetate Care | Tocopheryl Acetate | 0.20 |
| D | Ethanol | Alcohol | 15.00 |

Example B-4: Clear Sun Oil-Ethanol Spray SPF 50

| Phase | Ingredients | INCI | % by weight |
|---|---|---|---|
| A | Cetiol ® AB | C12-15 Alkyl Benzoate | 21.30 |
|   |  | C12-14 Aklyl Lactate | 10.00 |
|   | Cetiol ® C 5 | Coco-Caprylate | 16.00 |
|   | Cetiol ® CC | Dicaprylyl Carbonate | 10.00 |
|   | Cosmedia ® DC | Hydrogenated Dimer Dilinoleyl/-Dimethylcarbonate Copolymer | 2.00 |
|   | Uvinul ® MC 80 | Ethylhexyl Methoxycinnamate | 10.00 |
|   | Uvinul ® A Plus | Diethylamino Hydroxybenzoyl Hexyl Benzoate | 10.00 |
|   | Tinosorb ® S | Bis-Ethylhexyloxyphenol Methoxyphenyl Triazine | 3.50 |
|   | Uvinul ® T 150 | Ethylhexyl Triazone | 2.00 |
| B | Vitamin E-Acetate Care | Tocopheryl Acetate | 0.20 |
| C | Ethanol | Alcohol | 15.00 |

Example B-5: Clear Oil Spray SPF 30

| Phase | Ingredients | INCI | % by weight |
|---|---|---|---|
| A | Cetiol ® 868 | Ethylhexyl Stearate | 27.00 |
|   | Cetiol ® CC | Dicaprylyl Carbonate | 35.00 |
|   |  | Alkyl Oligolactate | 8.00 |
|   | Cosmedia ® DC | Hydrogenated Dimer Dilinoleyl/Dimethylcarbonate Copolymer | 2.00 |
|   | Uvinul ® MC 80 | Ethylhexyl Methoxycinnamate | 10.00 |
|   | Uvinul ® A Plus | Diethylamino Hydroxybenzoyl Hexyl Benzoate | 7.00 |
|   | Neo Heliopan OS | Ethylhexyl Salicylate | 5.00 |
|   | Tinosorb ® S | Bis-Ethylhexyloxyphenol Methoxyphenyl Triazine | 2.50 |
| B | Aerosil 200 | Silica | 3.50 |

Example B-6: Clear Oil Spray SPF 50

| Phase | Ingredients | INCI | % by weight |
|---|---|---|---|
| A | Cetiol ® 868 | Ethylhexyl Stearate | 27.00 |
|   | Cetiol ® AB | C12-15 Alkyl Benzoate | 20.00 |
|   | Cetiol ® C 5 | Coco-Caprylate | 15.00 |
|   |  | Alkyl Oligolactate | 8.00 |
|   | Cosmedia ® DC | Hydrogenated Dimer Dilinoleyl/Dimethylcarbonate Copolymer | 1.00 |
|   | Uvinul ® MC 80 | Ethylhexyl Methoxycinnamate | 10.00 |
|   | Uvinul ® A Plus | Diethylamino Hydroxybenzoyl Hexyl Benzoate | 10.00 |
|   | Tinosorb ® S | Bis-Ethylhexyloxyphenol Methoxyphenyl Triazine | 3.50 |
|   | Uvinul ® T 150 | Ethylhexyl Triazone | 2.00 |
| B | Aerosil 200 | Silica | 3.50 |

Example B-7: Clear Oil Gel SPF 30

| Phase | Ingredient | INCI | % by weight |
|---|---|---|---|
| A | Cetiol ® 868 | Ethylhexyl Stearate | 42.50 |
|   | Cetiol ® C 5 | Coco-Caprylate | 10.00 |
|   | Cetiol ® AB | C12-15 Alkyl Benzoate | 8.00 |
|   |  | Alkyl Oligolactate | 8.00 |
|   | Cosmedia ® DC | Hydrogenated Dimer Dilinoleyl/Dimethylcarbonate Copolymer | 2.00 |
|   | Uvinul ® MC 80 | Ethylhexyl Methoxycinnamate | 10.00 |
|   | Uvinul ® A Plus | Diethylamino Hydroxybenzoyl Hexyl Benzoate | 7.00 |
|   | Neo Heliopan OS (Symrise) | Ethylhexyl Salicylate | 5.00 |
|   | Tinosorb ® S | Bis-Ethylhexyloxyphenol Methoxyphenyl Triazine | 2.50 |
| B | Aerosil 200 | Silica | 5.00 |

Example B-8: W/Si Shake Well (BMDBM, OCR, Tinosorb A2B) SPF 30

| Phase | Ingredients | INCI | % by weight |
|---|---|---|---|
| A | Dehymuls ® LE | PEG-30 Dipolyhydroxystearate | 1.50 |
|   | Lameform ® TGI | Polyglyceryl-3 Diisostearate | 1.50 |
|   | Cetiol ® B | Dibutyl Adipate | 8.00 |
|   |  | Alkyl Oligolactate | 5.0 |
|   | Cetiol ® Sensoft | Propylheptyl Caprylate | 10.00 |
|   | Cetiol ® CC | Dicaprylyl Carbonate | 8.00 |
|   | Uvinul ® N 539T | Octocrylene | 7.00 |
|   | Parsol 1789 | Butyl Methoxydibenzoylmethane | 5.00 |
| B | Water, demin. | Aqua | 25.90 |
|   | Glycerin | Glycerin | 3.00 |
|   | Sodium Chloride | Sodium Chloride | 0.80 |
|   | Aerosil 200 | Silica | 0.60 |
| C | Silsoft 034 | Caprylyl Methicone | 5.00 |
|   | Xiameter PMX-200 Silicone Fluid 5CS | Dimethicone | 2.00 |
| D | Ethanol | Alcohol | 5.00 |
|   | Tinosorb ® M | Methylene Bis-Benzotriazolyl Tetramethylbutylphenol (nano), Aqua, Decyl Glucoside, Propylene Glycol, Xanthan Gum | 5.00 |
|   | Tinosorb ® A2B | Tris-Biphenyl Triazine (nano), Aqua, Decyl Glucoside, Butylene Glycol, Disodium Phosphate, Xanthan Gum | 3.00 |

Example B-8: W/Si Shake Well (BMDBM, OCR, Tinosorb A2B) SPF 30

| Phase | Ingredients | INCI | % by weight |
|---|---|---|---|
| | Tospearl A145 | Polymethylsilsesquioxane | 2.00 |
| | Orgasol 2002 D | Nylon-12 | 1.70 |
| | NAT COS | | |
| | Preservative | | qs |

Example B-9: W/Si Shake Well SPF 30

| Phase | Ingredients | INCI | % by weight |
|---|---|---|---|
| A | | Alkyl Oligolactate | 8.00 |
| | Cetiol ® CC | Dicaprylyl Carbonate | 10.00 |
| | Uvinul ® MC 80 | Ethylhexyl Methoxycinnamate | 10.00 |
| | Uvinul ® A Plus | Diethylamino Hydroxybenzoyl Hexyl Benzoate | 7.00 |
| | Tinosorb ® S | Bis-Ethylhexyloxyphenol Methoxyphenyl Triazine | 0.80 |
| B | Xiameter PMX-0245 Cyclopentasiloxane | Cyclopentasiloxane | 10.00 |
| | Silsoft 034 | Caprylyl Methicone | 10.00 |
| | KF-6100 | Polyglyceryl-3 Disiloxane Dimethicone | 3.00 |
| C | Water, demin. | Aqua | 22.50 |
| | Butylene Glycol | Butylene Glycol | 3.00 |
| | Sodium Chloride | Sodium Chloride | 1.00 |
| | DN-Age ™ PW LS 9827 | Maltodextrin, Cassia Alata Leaf Extract | 1.00 |
| | Edeta ® BD | Disodium EDTA | 0.20 |
| D | Ethanol | Alcohol | 7.00 |
| | Tospearl 3000AG | Polymethylsilsesquioxane | 3.00 |
| | Orgasol Caresse | Polyamide-5 | 2.00 |
| | Osmogeline ™ | Aqua, Algae Extract, Citric Acid | 1.00 |
| | Parfum Sun Spray | Parfum | 0.50 |
| | Preservative | | qs |

Example B-10: O/W Lotion (without OMC, Tinosorb S Aqua) SPF 50+

| Phase | Ingredients | INCI | % by weight |
|---|---|---|---|
| A | Eumulgin ® Prisma | Disodium Cetearyl Sulfosuccinate | 3.00 |
| | | Alkyl Oligolactate | 10.00 |
| | Cetiol ® CC | Dicaprylyl Carbonate | 8.00 |
| | Cetiol ® AB | C12-15 Alkyl Benzoate | 10.00 |
| | Uvinul ® A Plus | Diethylamino Hydroxybenzoyl Hexyl Benzoate | 8.00 |
| | Uvinul ® T 150 | Ethylhexyl Triazone | 3.00 |
| | Tinosorb ® S | Bis-Ethylhexyloxyphenol Methoxyphenyl Triazine | 2.00 |
| B | Water, demin. | Aqua | 34.00 |
| | Edeta ® BD | Disodium EDTA | 0.20 |
| | Amphisol K | Potassium Cetyl Phosphate | 0.50 |
| | Keltrol CG-T | Xanthan Gum | 0.50 |
| C | Xiameter PMX-0246 Cyclohexasiloxane | Cyclohexasiloxane | 4.00 |
| | KSG-16 | Dimethicone, Dimethicone/Vinyl Dimethicone Crosspolymer | 2.00 |
| D | Dry-Flo AF | Corn Starch Modified | 2.00 |
| E | Water, demin. | Aqua | 6.00 |
| | Eusolex 232 | Phenylbenzimidazole Sulfonic Acid | 3.00 |
| | Tris Amino Ultra Pur | Trometamine | 1.80 |
| F | Tinosorb ® S Aqua | Aqua, Bis-Ethylhexyloxyphenol Methoxyphenyl Triazine, Polymethyl Methacrylate, Sodium Laureth Sulfate, Aminomethyl Propanol | 10.00 |
| | Preservative | | qs |

Example B-11: O/W Lotion (Without OMC, Tinosorb M) SPF 30

| Phase | Ingredients | INCI | % by weight |
|---|---|---|---|
| A | Emulgade ® Sucro | Sucrose Polystearate, Hydrogenated Polyisobutene | 3.00 |
| | Eumulgin ® Prisma | Disodium Cetearyl Sulfosuccinate | 1.00 |
| | Lanette ® O | Cetearyl Alcohol | 1.00 |
| | Cetiol ® B | Dibutyl Adipate | 10.00 |
| | | Alkyl Oligolactate | 5.00 |
| | Uvinul ® A Plus | Diethylamino Hydroxybenzoyl Hexyl Benzoate | 4.50 |
| | Uvinul ® T 150 | Ethylhexyl Triazone | 2.50 |
| B | Water, demin. | Aqua | 59.10 |
| | Glycerin | Glycerin | 3.00 |
| | Keltrol CG-RD | Xanthan Gum | 0.50 |
| | Edeta ® BD | Disodium EDTA | 0.20 |
| C | Eusolex 232 | Phenylbenzimidazole Sulfonic Acid | 2.20 |
| | Water, demin. | Aqua | 3.00 |
| | Tris Amino Ultra Pur | Trometamine | qs |
| D | Tinosorb ® M | Methylene Bis-Benzotriazolyl Tetramethylbutylphenol (nano), Aqua, Decyl Glucoside, Propylene Glycol, Xanthan Gum | 4.00 |
| | Orgasol Caresse | Polyamide-5 | 1.00 |
| | Perfume | Parfum | qs |
| | Preservative | | qs |

Example B-12: O/W Cream (Without OMC, Tinosorb M) SPF 50+

| Phase | Ingredients | INCI | % by weight |
|---|---|---|---|
| A | Emulgade ® Sucro | Sucrose Polystearate, Hydrogenated Polyisobutene | 5.00 |
| | Eumulgin ® Prisma | Disodium Cetearyl Sulfosuccinate | 2.00 |
| | Lanette ® O | Cetearyl Alcohol | 1.00 |
| | | Alkyl Oligolactate | 12.00 |
| | Cetiol ® AB | C12-15 Alkyl Benzoate | 12.00 |
| | Cetiol ® CC | Dicaprylyl Carbonate | 4.00 |
| | Uvinul ® A Plus | Diethylamino Hydroxybenzoyl Hexyl Benzoate | 6.00 |
| | Uvinul ® T 150 | Ethylhexyl Triazone | 3.50 |
| | Tinosorb ® S | Bis-Ethylhexyloxyphenol Methoxyphenyl Triazine | 2.50 |
| B | Water, demin. | Aqua | 27.80 |
| | Glycerin | Glycerin | 3.00 |
| | Keltrol CG-RD | Xanthan Gum | 0.50 |
| | Edeta ® BD | Disodium EDTA | 0.20 |

Example B-12: O/W Cream (Without OMC, Tinosorb M) SPF 50+

| Phase | Ingredients | INCI | % by weight |
|---|---|---|---|
| C | Eusolex 232 | Phenylbenzimidazole Sulfonic Acid | 3.50 |
|   | Water, demin. | Aqua | 6.00 |
|   | Tris Amino Ultra Pur | Tromethamine | qs |
| D | Tinosorb ® M | Methylene Bis-Benzotriazolyl Tetramethylbutylphenol (nano), Aqua, Decyl Glucoside, Propylene Glycol, Xanthan Gum | 8.00 |
|   | Techpolymer MBP 8 | Polymethyl Methacrylate | 2.00 |
|   | Orgasol Caresse | Polyamide-5 | 1.00 |
|   | Perfume | Parfum | qs |
|   | Preservative |  | qs |

Example B-13: O/W Soft Cream (OMC) SPF 50

| Phase | Ingredients | INCI | % by weight |
|---|---|---|---|
| A | Emulgade ® Sucro | Sucrose Polystearate, Hydrogenated Polyisobutene | 4.50 |
|   | Eumulgin ® BA 25 | Beheneth-25 | 2.00 |
|   |   | Alkyl Oligolactate | 8.00 |
|   | Cetiol ® AB | C12-15 Alkyl Benzoate | 10.00 |
|   | Lanette ® O | Cetearyl Alcohol | 1.00 |
|   | Uvinul ® MC 80 | Ethylhexyl Methoxycinnamate | 10.00 |
|   | Uvinul ® A Plus | Diethylamino Hydroxybenzoyl Hexyl Benzoate | 10.00 |
|   | Uvinul ® T 150 | Ethylhexyl Triazone | 3.00 |
|   | Tinosorb ® S | Bis-Ethylhexyloxyphenol Methoxyphenyl Triazine | 2.50 |
| B | Water, demin, | Aqua | 39.30 |
|   | Glycerin | Glycerin | 3.00 |
|   | Keltrol CG-RD | Xanthan Gum | 0.50 |
|   | Edeta ® BD | Disodium EDTA | 0.20 |
| C | Techpolymer MBP 8 | Polymethyl Methacrylate | 2.00 |
|   | Orgasol Caresse | Polyamide-5 | 1.00 |
|   | Preservative |  | qs |
|   | Xiameter PMX-0246 Cyclohexasiloxane | Cyclohexasiloxane | 3.00 |

Example B-14: O/W Soft Cream (OMC, Tinosorb M) SPF 50

| Phase | Ingredient | INCI | % by weight |
|---|---|---|---|
| A | Emulgade ® Sucro | Sucrose Polystearate, Hydrogenated Polyisobutene | 4.50 |
|   | Eumulgin ® BA 25 | Beheneth-25 | 2.00 |
|   |   | Alkyl Oligolactate | 8.00 |
|   | Cetiol ® AB | C12-15 Alkyl Benzoate | 10.00 |
|   | Lanette ® O | Cetearyl Alcohol | 1.00 |
|   | Uvinul ® MC 80 | Ethylhexyl Methoxycinnamate | 10.00 |
|   | Uvinul ® a Plus | Diethylamino Hydroxybenzoyl Hexyl Benzoate | 8.00 |
|   | Uvinul ® T 150 | Ethylhexyl Triazone | 2.50 |
| B | Water, demin. | Aqua | 37.30 |
|   | Glycerin | Glycerin | 3.00 |
|   | Keltrol CG-RD | Xanthan Gum | 0.50 |
|   | Edeta ® BD | Disodium EDTA | 0.20 |
| C | Tinosorb ® M | Methylene Bis-Benzotriazolyl Tetramethylbutylphenol (nano), Aqua, Decyl Glucoside, Propylene Glycol, Xanthan Gum | 7.00 |
|   | Techpolymer MBP 8 | Polymethyl Methacrylate | 2.00 |
|   | Preservative |  | qs |
|   | Orgasol Caresse | Polyamide-5 | 1.00 |
|   | Xiameter PMX-0246 Cyclohexasiloxane | Cyclohexasiloxane | 3.00 |

Example B-15: O/W Soft Cream (without OMC, TiO2) SPF 50

| Phase | Ingredients | INCI | % by weiqht |
|---|---|---|---|
| A | Emulgade ® Sucro | Sucrose Polystearate, Hydrogenated Polyisobutene | 4.50 |
|   | Eumulgin ® Prisma | Disodium Cetealyl Sulfosuccinate | 2.00 |
|   | Cetiol ® AB | C12-15 Alkyl Benzoate | 10.00 |
|   |   | Alkyl Oligolactate | 10.00 |
|   | Cetiol ® CC | Dicaprylyl Carbonate | 3.00 |
|   | Lanette ® O | Cetearyl Alcohol | 1.00 |
|   | Uvinul ® A Plus | Diethylamino Hydroxybenzoyl Hexyl Benzoate | 4.50 |
|   | Uvinul ® T 150 | Ethylhexyl Triazone | 3.00 |
|   | STR-100A-LP | Titanium Dioxide (nano), Hydrated Silica, Dimethicone/Methicone Copolymer, Aluminum Hydroxide | 2.15 |
|   | Tinosorb ® S | Bis-Ethylhexyloxyphenol Methoxyphenyl Triazine | 2.00 |
| B | Water, demin. | Aqua | 38.65 |
|   | Glycerin | Glycerin | 3.00 |
|   | Keltrol CG-RD | Xanthan Gum | 0.50 |
|   | Edeta ® BD | Disodium EDTA | 0.20 |
| C | Eusolex 232 | Phenylbenzimidazole Sulfonic Acid | 3.50 |
|   | Water, demin, | Aqua | 5.00 |
|   | Tris Amino Ultra Pur | Tromethamine | 2.00 |
| D | Techpolymer MBP 8 | Polymethyl Methacrylate | 2.00 |
|   | Orgasol Caresse | Polyamide-5 | 1.00 |
|   | Preservative |  | qs |

Example B-16: Polymeric Emulsion (Tinosorb A2B) SPF 50

| Phase | Ingredients | INCI | % by weight |
|---|---|---|---|
| A | Eumulgin ® B 2 | Ceteareth-20 | 2.00 |
|   | Cetiol ® CC | Dicaprylyl Carbonate | 11.00 |
|   | Cetiol ® AB | C12-15 Alkyl Benzoate | 4.00 |
|   |   | Alkyl Oligolactate | 4.00 |
|   | Cetiol ® C 5 | Coco-Caprylate | 8.00 |
|   | Tinosorb ® S | Bis-Ethylhexyloxyphenol Methoxyphenyl Triazine | 2.50 |
|   | Uvinul ® T 150 | Ethylhexyl Triazone | 2.00 |
| B | Water, demin. | Aqua | 32.10 |
|   | Glycerin | Glycerin | 3.00 |
|   | Keltrol CG-RD | Xanthan Gum | 0.30 |
|   | Edeta ® BD | Disodium EDTA | 0.20 |
| C | Tinovis ® ADE | Sodium Acrylates Copolymer, Hydrogenated Polydecene, PPG-1 Trideceth-6 | 0.90 |
| D | Cetiol ® Ultimate | Undecane, Tridecane | 5.00 |
| E | Tinosorb ® M | Methylene Bis-Benzotriazolyl Tetramethylbutylphenol (nano), Aqua, Decyl Glucoside, Propylene Glycol, Xanthan Gum | 12.00 |

Example B-16: Polymeric Emulsion (Tinosorb A2B) SPF 50

| Phase | Ingredients | INCI | % by weight |
|---|---|---|---|
| | Tinosorb ® A2B | Tris-Biphenyl Triazine (nano), Aqua, Decyl Glucoside, Butylene Glycol, Disodium Phosphate, Xanthan Gum | 8.00 |
| F | Lipofructyl ™ Argan LS 9779 | *Argania Spinosa* Kernel Oil | 2.50 |
| | Melhydran ™ LS 4420 | Honey Extract | 2.50 |
| | Preservative | | qs |
| | Perfume | Parfum | qs |
| | Sodium Hydroxide (30% solution) | Sodium Hydroxide | qs |

Example B-17: O/W Polymeric Emulsion SPF 50

| Phase | Ingredients | INCI | % by weight |
|---|---|---|---|
| A | Cetiol ® CC | Dicaprylyl Carbonate | 5.00 |
| | | Alkyl Oligolactate | 3.00 |
| | Uvinul ® MC 80 | Ethylhexyl Methoxycinnamate | 10.00 |
| | Uvinul ® A Plus | Diethlamino Hydroxybenzoyl Hexyl Benzoate | 8.00 |
| | Neo Heliopan OS | Ethylhexyl Salicylate | 5.00 |
| | Uvinul ® T 150 | Ethylhexyl Triazone | 2.50 |
| B | Water, demin. | Aqua | 41.00 |
| | 1,2 Butanediol | Butylene Glycol | 2.50 |
| | Tinovis ® GTC | Acrylates/Beheneth-25 Methacrylate Copolymer | 2.00 |
| C | Sodium Hydroxide (30% solution) | Sodium Hydroxide | qs |
| D | Tinosorb ® M | Methylene Bis-Benzotriazolyl Tetramethylbutylphenol (nano), Aqua, Decyl Glucoside, Propylene Glycol, Xanthan Gum | 4.00 |
| E | Ethanol | Alcohol | 10.00 |
| | Xiameter PMX-0246 Cyclohexasiloxane | Cyclohexasiloxane | 4.00 |
| | Orgasol 4000 EXD NAT COS Caresse | Nylon-6/12 | 2.00 |
| | Tospearl A145 | Polymethylsilsesquioxane | 1.00 |

Example B-18: O/W Cream SPF 30

| Phase | Ingredients | INCI | % by weight |
|---|---|---|---|
| A | Eumulgin ® SG | Sodium Stearoyl Glutamate | 2.00 |
| | Lanette ® 18 | Stearyl Alcohol | 1.00 |
| | Cetiol ® CC | Dicaprylyl Carbonate | 8.00 |
| | Cetiol ® B | Dibutyl Adipate | 5.00 |
| | Cetiol ® AB | C12-15 Alkyl Benzoate | 5.00 |
| | | Alkyl Oligolactate | 3.00 |
| | Uvinul ® A Plus | Diethylamino Hydroxybenzoyl Hexyl Benzoate | 10.00 |
| | Uvinul ® T 150 | Ethylhexyl Triazone | 3.00 |
| | Tinosorb ® S | Bis-Ethylhexyloxyphenol Methoxyphenyl Triazine | 3.00 |
| B | Water, demin. | Aqua | 54.20 |
| | Glycerin | Glycerin | 3.00 |
| | Cosmedia ® SP | Sodium Polyacrylate | 0.60 |
| | Keltrol CG-RD | Xanthan Gum | 0.50 |
| | Edeta ® BD | Disodium EDTA | 0.20 |
| C | Orgasol Caresse | Polyamide-5 | 1.50 |
| | Preservative | | qs |

Example B-19: O/W emulsion Spray SPF 50

| Phase | Ingredients | INCI | % by weight |
|---|---|---|---|
| A | Eumulgin ® B 2 | Ceteareth-20 | 1.50 |
| | | Alkyl Oligolactate | 8.00 |
| | Cetiol ® AB | C12-15 Alkyl Benzoate | 10.00 |
| | Cetiol ® CC | Dicaprylyl Carbonate | 3.00 |
| | Uvinul ® A Plus | Diethylamino Hydroxybenzoyl Hexyl Benzoate | 8.00 |
| | Uvinul ® T 150 | Ethylhexyl Triazone | 3.00 |
| | Tinosorb ® S | Bis-Ethylhexyloxyphenol Methoxyphenyl Triazine | 2.00 |
| B | Water, demin. | Aqua | 38.20 |
| | Tris Amino Ultra Pur | Trometamine | 0.30 |
| | Dermofeel PA3 | Sodium Phytate | 0.10 |
| | Tinovis ® GTC | Acrylates/Beheneth-25 Methacrylate Copolymer | 1.50 |
| C | Water, demin. | Aqua | 10.00 |
| | Tris Amino Ultra Pur | Trometamine | 1.40 |
| | Eusolex 232 | Phenylbenzimidazole Sulfonic Acid | 3.00 |
| D | Tinosorb ® S Aqua | Aqua, Bis-Ethylhexyloxyphenol Methoxyphenyl Triazine, Polymethyl Methacrylate, Sodium Laureth Sulfate, Aminomethyl Propanol | 10.00 |
| | Perfume | Parfum | qs |
| | Preservative | | qs |

Example B-20: O/W emulsion Spray SPF 50

| Phase | Ingredients | INCI | % by weight |
|---|---|---|---|
| A | Eumulgin ® VL 75 | Lauryl Glucoside, Polyglyceryl-2 Dipolyhydroxystearate, Glycerin | 6.00 |
| | | Alkyl Oligolactate | 8.00 |
| | Cetiol ® AB | C12-15 Alkyl Benzoate | 12.00 |
| | Cetiol ® CC | Dicaprylyl Carbonate | 3.00 |
| | Uvinul ® A Plus | Diethylamino Hydroxybenzoyl Hexyl Benzoate | 10.00 |
| | Uvinul ® T 150 | Ethylhexyl Triazone | 3.00 |
| | Tinosorb ® S | Bis-Ethylhexyloxyphenol Methoxyphenyl Triazine | 2.00 |
| B | Water, demin. | Aqua | 37.40 |
| | Dermofeel PA3 | Sodium Phytate | 0.10 |
| | Avicel PC 611 | Microcrystalline Cellulose | 1.20 |
| C | Water, demin. | Aqua | 8.00 |
| | Eusolex 232 | Phenylbenzimidazole Sulfonic Acid | 3.00 |
| | Neutrol ® TE | Tetrahydroxypropyl Ethylenediamine | 3.30 |
| D | Tinosorb ® S Aqua | Aqua, Bis-Ethylhexyloxyphenol Methoxyphenyl Triazine, Polymethyl Methacrylate, Sodium Laureth Sulfate, Aminomethyl Propanol | 5.00 |
| | Perfume | Perfume | qs |
| | Preservative | | qs |

Example B-21: O/W Emulsion Spray Emulsifier Free SPF 50

| Phase | Ingredients | INCI | % by weight |
|---|---|---|---|
| A | Cetiol CC | Dicaprylyl Carbonate | 5.00 |
| | | Alkyl Oligolactate | 10.00 |
| | Uvinul ® A Plus | Diethylamino Hydroxybenzoyl Hexyl Benzoate | 2.50 |
| | Uvinul ® T 150 | Ethylhexyl Triazone | 2.00 |
| | Tinosorb ® S | Bis-Ethylhexyloxyphenol Methoxyphenyl Triazine | 1.50 |

Example B-21: O/W Emulsion Spray Emulsifier Free SPF 50

| Phase | Ingredients | INCI | % by weight |
|---|---|---|---|
| B | Water, demin. | Aqua | 68.10 |
|  | Glycerin | Glycerin | 3.00 |
|  | Luvigel ® FIT UP | Acrylates/C10-30 Alkyl Methacrylate Copolymer | 0.70 |
|  | Avicel PC 611 | Microcrystalline Cellulose | 0.70 |
| C | Water, demin. | Aqua | 5.00 |
|  | Eusolex 232 | Phenylbenzimidazole Sulfonic Acid | 1.50 |
|  | Tris Amino Ultra Pur | Tromethamine | qs |
| D | Preservative |  | qs |

Example B-22: W/O Lotion SPF 50

| Phase | Ingredients | INCI | % by weight |
|---|---|---|---|
| A | Dehymuls ® PGPH | Polyglyceryl-2 Dipolyhydroxystearate | 3.00 |
|  | Lameform ® TGI | Polyglyceryl-3 Diisostearate | 1.00 |
|  | Cetiol ® AB | C12-15 Alkyl Benzoate | 5.00 |
|  |  | Alkyl Oligolactate | 5.00 |
|  | Cetiol ® CC | Dicaprylyl Carbonate | 3.00 |
|  | Magnesium Stearate | Magnesium Stearate | 1.00 |
|  | Uvinul ® MC 80 | Ethylhexyl Methoxycinnamate | 10.00 |
|  | Uvinul ® A Plus | Diethylamino Hydroxybenzoyl Hexyl Benzoate | 10.00 |
|  | Uvinul ® T 150 | Ethylhexyl Triazone | 2.50 |
|  | Tinosorb ® S | Bis-Ethylhexyloxyphenol Methoxyphenyl Triazine | 2.20 |
| B | Water, demin. | Aqua | 48.30 |
|  | Glycerin | Glycerin | 3.00 |
|  | Magnesium Sulfate Heptahydrate | Magnesium Sulfate | 1.00 |
| C | Xiameter PMX-0345 Cyclosiloxane Blend | Cyclopentasiloxane, Cyclohexasiloxane | 5.00 |
|  | Preservative |  | qs |

Example B-23: W/O Cream Particulates Only SPF 50

| Phase | Ingredients | INCI | % by weight |
|---|---|---|---|
| A | Dehymuls ® LE | PEG-30 Dipolyhydroxystearate | 1.50 |
|  | Cetiol ® MM | Myristyl Myristate | 2.00 |
|  | Cetiol ® CC | Dicaprylyl Carbonate | 25.00 |
|  |  | Alkyl Oligolactate | 4.00 |
|  | MT-100 Z | Titanium Dioxide (nano), Aluminum Hydroxide, Stearic Acid | 6.00 |
| B | Water, demin. | Aqua | 30.40 |
|  | Glycerin | Glycerin | 4.00 |
|  | Magnesium Sulfate Heptahydrate | Magnesium Sulfate | 0.80 |
|  | Keltrol CG-T | Xanthan Gum | 0.30 |
| C | Tinosorb ® A2B | Tris-Biphenyl Triazine (nano), Aqua, Decyl Glucoside, Butylene Glycol, Disodium Phosphate, Xanthan Gum | 10.00 |
|  | Tinosorb ® M | Methylene Bis-Benzotriazolyl Tetramethylbutylphenol (nano), Aqua, Decyl Glucoside, Propylene Glycol, Xanthan Gum | 14.00 |
| D | Techpolymer MBP 8 | Polymethyl Methacrylate | 2.00 |
| E | Preservative |  | qs |

Example B-24: O/W BB Cream SPF 30

| Phase | Ingredients | INCI | % by weight |
|---|---|---|---|
| A | Water, demin. | Aqua | 38.00 |
|  | Rheocare ® XG | Xanthan Gum | 0.40 |
|  | Veegum Ultra | Magnesium Aluminum Silicate | 1.00 |
|  | Phenonip XB | Phenoxyethanol, Methylparaben, Ethylparaben, Propylparaben | 1.00 |
| B | Butylene Glycol | Butylene Glycol | 5.00 |
|  | SunCROMA Titanium Dioxide C47-051 | CI 77891 | 5.00 |
| C | Eumulgin ® BA 25 | Beheneth-25 | 3.00 |
|  | Lameform ® TGI | Polyglyceryl-3 Diisostearate | 1.50 |
|  | Cutina ® PES | Pentaerythrityl Distearate | 1.00 |
|  | Uvinul ® MC 80 | Ethylhexyl Methoxycinnamate | 9.00 |
|  | Uvinul ® A Plus | Diethylamino Hydroxybenzoyl Hexyl Benzoate | 5.00 |
|  | Tinosorb ® S | Bis-Ethylhexyloxyphenol Methoxyphenyl Triazine | 2.00 |
|  | Cosmedia ® DC | Hydrogenated Dimer Dilinoleyl/Dimethylcarbonate Copolymer | 1.00 |
|  |  | C12-15 Alkyl Lactate | 6.00 |
|  | Cetiol ® AB | C12-15 Alkyl Benzoate | 10.00 |
| D | Chione ™ M SVA | Synthetic Fluorphlogopite, Lauroyl Lysine | 1.00 |
|  | Chroma-Lite ® Yellow CL4502 | Mica, Bismuth Oxychloride, Iron Oxides | 4.00 |
|  | Chroma-Lite ® Red CL4506 | Mica, Bismuth Oxychloride, Iron Oxides | 1.00 |
|  | Chroma-Lite ® Black CL4498 | Mica, Bismuth Oxychloride, Iron Oxides | 0.40 |
|  | Chione ™ HD Crisp Gold S230V | Synthetic Fluorphlogopite, Titanium Dioxide | 3.00 |
| E | Hyalufix ™ GL A00102 | Aqua, Butylene Glycol, Alpina Galanga Extract, Pentylene Glycol, Xanthan Gum, Caprylic/Capric Triglyceride | 1.00 |
|  | Xiameter PMX-0345 Cyclosiloxane Blend | Cyclopentasiloxane, Cyclohexasiloxane | 0.50 |
|  | Perfume | Parfum | 0.20 |

Example B-25: Water free Stick SPF 30

| Phase | Ingredients | INCI | % by weight |
|---|---|---|---|
| A | Cetiol ® CC | Dicaprylyl Carbonate | 11.20 |
|  |  | Alkyl Oligolactate | 4.00 |
|  | Cetiol ® Sensoft | Propylheptyl Caprylate | 4.00 |
|  | Cosmedia ® DC | Hydrogenated Dimer Dilinoleyl/Dimethylcarbonate Copolymer | 1.00 |
|  | Z-Cote ® | Zinc Oxide (nano) | 10.00 |
|  | Uvinul ® MC 80 | Ethylhexyl Methoxycinnamate | 5.50 |
|  | Uvinul ® A Plus | Diethylamino Hydroxybenzoyl Hexyl Benzoate | 5.00 |
|  | STR-100A-LP | Titanium Dioxide (nano), Hydrated Silica, Dimethicone/Methicone Copolymer, Aluminum Hydroxide | 3.90 |
| B | Cutina ® HR Powder | Hydrogenated Castor Oil | 5.00 |
|  | Lanette ® O | Cetearyl Alcohol | 5.00 |
|  | Cutina ® PES | Pentaerythrityl Distearate | 4.00 |
|  | Xiameter PMX-0245 Cyclopentasiloxane | Cyclopentasiloxane | 7.00 |
|  | Talc | Talc | 34.40 |
|  | Protectol ® PE | Phenoxyethanol | qs |

Example B-26: Lip Stick SPF 15

| Phase | Ingredients | INCI | % by weight |
|---|---|---|---|
| A | Plandool-G | Bis-Behenyl/Isostearyl/Phytosteryl Dimer Dilinoleyl Dimer Dilinoleate | 7.00 |
|  | Candelilla Wax | Candelilla Cera | 5.00 |
|  | Carnauba Wax T1 | Carnauba Cera | 4.00 |
|  | Performa V 1608 Polymer | C30-38 Olefin/Isopropyl Maleate/MA Copolymer | 4.00 |
|  | Performa V 343 | Synthetic Wax | 4.00 |
| B | Myritol ® 318 | Caprylic/Capric Triglyceride | 20.50 |
|  |  | Alkyl Oligolactate | 4.00 |
|  | Uvinul ® MC 80 | Ethylhexyl Methoxycinnamate | 5.50 |
|  | Tinosorb ® S | Bis-Ethylhexyloxyphenol Methoxyphenyl Triazine | 1.00 |
|  | Uvinul ® A Plus | Diethylamino Hydroxybenzoyl Hexyl Benzoate | 3.00 |
| C | Nikkol DGTIS | Polyglyceryl-2 Triisostearate | 14.00 |
|  | Crodamol TTIS | Trimethylolpropane Triisostearate | 10.00 |
| D | Floraesters 30 | Jojoba Esters | 12.00 |
| E | MultiReflections™ Soft Sparkle Rose 480P | Mica, Titanium Dioxide, Silica | 2.00 |
|  | Gemtone ® Tan Opal G005 | Mica, Iron Oxides, Titanium Dioxide | 2.00 |
|  | Cloisonne ® Super Rouge 450Z | Mica, Iron Oxides | 2.00 |

Example B-27: O/W Cream (BMDBM, Tinosorb A2B, Tinosorb M) SPF 50

| Phase | Ingredients | INCI | % by weight |
|---|---|---|---|
| A | Eumulgin ® Prisma | Disodium Cetearyl Sulfosuccinate Alkyl Oligolactate | 1.00 5.00 |
|  | Cetiol ® CC | Dicaprylyl Carbonate | 10.00 |
|  | Cetiol ® AB | C12-15 Alkyl Benzoate | 10.00 |
|  | Lanette ® O | Cetearyl Alcohol | 2.50 |
|  | Cutina ® HVG | Hydrogenated Vegetable Glycerides | 2.00 |
|  | Sensiva SC 5 | Ethylhexylglycerin | 0.50 |
|  | Parsol 1789 | Butyl Methoxydibenzoylmethane | 3.50 |
|  | Uvinul ® T 150 | Ethylhexyl Triazone | 2.50 |
|  | Tinosorb ® S | Bis-Ethylhexyloxyphenol Methoxyphenyl Triazine | 2.50 |
| B | Water, demin. | Aqua | 37.15 |
|  | Glycerin | Glycerin | 3.00 |
|  | Cosmedia ® SP | Sodium Polyacrylate | 1.00 |
|  | Edeta ® BD | Disodium EDTA | 0.20 |
|  | Rheocare ® XG (Europe only) | Xanthan Gum | 0.15 |
| C | Eusolex 232 | Phenylbenzimidazole Sulfonic Acid | 1.00 |
|  | Water, demin. | Aqua | 5.00 |
|  | Tris Amino Ultra Pur | Tromethamine | qs |
| D | Orgasol Caresse | Polyamide-5 | 0.50 |
|  | Orgasol 2002 D NAT COS | Nylon-12 | 0.50 |
|  | Preservative |  | qs |

Example B-28: O/W Polymeric Emulsion (BMDBM, Tinosorb S, Tinosorb M) SPF 30

| Phase | Ingredients | INCI | % by weight |
|---|---|---|---|
| A | Eumulgin ® Prisma | Disodium Cetearyl Sulfosuccinate | 0.50 |
|  | Cetiol ® AB | C12-15 Alkyl Benzoate | 12.00 |
|  | Cetiol ® CC | Dicaprylyl Carbonate | 4.00 |
|  |  | Alkyl Oligolactate | 8.00 |
|  | Sensiva SC 50 | Ethylhexylglycerin | 0.50 |
|  | Uvinul ® T 150 | Ethylhexyl Triazone | 3.50 |
|  | Parsol 1789 | Butyl Methoxydibenzoylmethane | 3.00 |
|  | Tinosorb ® S | Bis-Ethylhexyloxyphenol Methoxyphenyl Triazine | 2.00 |
| B | Water, demin. | Aqua | 41.95 |
|  | Butylene Glycol | Butylene Glycol | 6.00 |
|  | Glycerin | Glycerin | 1.00 |
|  | Protectol ® PE | Phenoxyethanol | 1.00 |
|  | Edeta ® BX Powder | Tetrasodium EDTA | 0.20 |
|  | Keltrol RD | Xanthan Gum | 0.20 |
|  | Carbopol Ultrez 10 Polymer | Carbomer | 0.20 |
|  | Pemulen TR-2 Polymeric Emulsifier | Acrylates/C10-30 Alkyl Acrylate Crosspolymer | 0.15 |
| C | AMP-Ultra PC 2000 | Aminomethyl Propanol | qs |
| D | Tinosorb ® M | Methylene Bis-Benzotriazolyl Tetramethylbutylphenol (nano), Aqua, Decyl Glucoside, Propylene Glycol, Xanthan Gum | 6.00 |
|  | Water, demin. | Aqua | 4.00 |
| E | Ethanol | Alcohol | 5.00 |
|  | Menthol | Menthol | 0.80 |

Example B-29: Anhydrous O/Si Mousse SPF 30

| Phase | Ingredients | INCI | % by weight |
|---|---|---|---|
| A | Olivem 900 | Sorbitan Olivate | 16.00 |
|  |  | C12-14 Alkyl Latate | 6.00 |
|  | Uvinul ® MC 80 | Ethylhexyl Methoxycinnamate | 9.00 |
|  | Uvinul ® A Plus | Diethylamino Hydroxybenzoyl Hexyl Benzoate | 5.50 |
|  | Neo Heliopan OS | Ethylhexyl Salicylate | 5.00 |
|  | Tinosorb ® S | Bis-Ethylhexyloxyphenol Methoxyphenyl Triazine | 2.00 |
| B | Belsil TMS 803 Silicone Resin | Trimethylsiloxysilicate | 4.00 |
|  | Tospearl A145 | Polymethylsilsesquioxane | 0.70 |
|  | Silsoft 034 | Caprylyl Methicone | 0.30 |
| C | HDK H15 | Silica Dimethyl Silylate | 1.30 |
| D | Belsil REG 1100 Silicone elastomer resin gel | Dimethicone, Vinyldimethyl, Trimethylsiloxysilicate, Dimethicone Crosspolymer | 22.00 |
|  | Belsil RG 100 | Cyclopentasiloxane, Dimethicone/Vinyltrimethylsiloxysilicate Crosspolymer | 18.50 |

Example B-29: Anhydrous O/Si Mousse SPF 30

| Phase | Ingredients | INCI | % by weight |
|---|---|---|---|
| | Xiameter PMX-0245 Cyclopentasiloxane | Cyclopentasiloxane | 6.30 |
| | Belsil DM 0.65 | Disiloxane | 3.40 |

Example B-30: Anhydrous O/Si Gel SPF 20

| Phase | Ingredients | INCI | % by weight |
|---|---|---|---|
| A | Dow Corning EL-7040 Hydro Elastomer Blend | Caprylyl Methicone, PEG-12 Dimethicone/PPG-20 Crosspolymer | 58.50 |
| | Dow Corning 5200 Formulation Aid | Lauryl PEG/PPG-18/18 Methicone | 6.00 |
| | Abil WE 09 | Polyglyceryl-4 Isostearate, Cetyl PEG/PPG-10/1 Dimethicone, Hexyl Laurate | 5.00 |
| | Xiameter PMX-0245 Cyclopenta-siloxane | Cyclopentasiloxane | 1.00 |
| B | Cetiol ® AB | C12-15 Alkyl Benzoate | 11.00 |
| | | Alkyl Oligolactate | 5.00 |
| | Uvinul ® MC 80 | Ethylhexyl Methoxycinnamate | 6.00 |
| | Uvinul ® A Plus | Diethylamino Hydroxybenzoyl Hexyl Benzoate | 5.00 |
| | Tinosorb ® S | Bis-Ethylhexyloxyphenol Methoxyphenyl Triazine | 1.00 |
| | Orgasol Caresse | Polyamide-5 | 1.00 |
| | Butylene Glycol | Butylene Glycol | 0.50 |

The invention claimed is:

1. A solubilizing agent for an organic UV filter corresponding to formula (1)

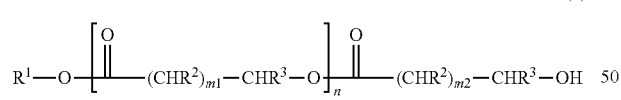

wherein $R^1$ is hydrogen; or a linear or branched $C_1$-$C_{30}$ aliphatic hydrocarbon residue comprising 0, 1, 2 or 3 double bonds;

$R^2$ independently from each other are hydrogen; methyl; ethyl; —OH; —COOR$^4$; —CH$_2$—OH; or —CH$_2$—COOR$^4$;

$R^4$ is hydrogen; or a linear or branched $C_1$-$C_{30}$ aliphatic hydrocarbon residue comprising 0, 1, 2 or 3 double bonds;

$R^3$ independently from each other are hydrogen; methyl; ethyl; —OH; —COOR$^5$; —CH$_2$—OH; or —CH$_2$—COOR$^5$;

$R^5$ is hydrogen; or a linear or branched $C_1$-$C_{30}$ aliphatic hydrocarbon residue comprising 0, 1, 2 or 3 double bonds;

n is at least 0.1 on average;

m1 and m2 independently from each other are 0 or 1;

with the proviso, that at least one of the radicals $R^1$, $R^4$ or $R^5$ represent a linear or branched $C_1$-$C_{30}$ aliphatic hydrocarbon residue comprising 0, 1, 2 or 3 double bonds, wherein the organic UV filter is selected from the group consisting of (B1) benzophenone derivatives corresponding to the formula

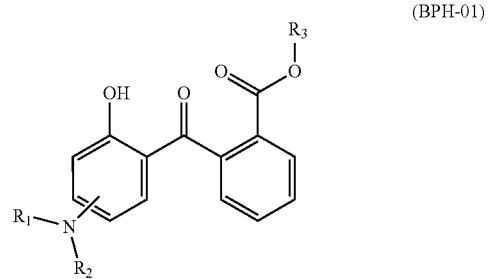

(BPH-01)

wherein $R_1$ and $R_2$ independently from each other are hydrogen; $C_1$-$C_{20}$alkyl; $C_3$-$C_{10}$cycloalkyl; or $C_3$-$C_{10}$cycloalkenyl, wherein the radicals $R_1$ and $R_2$ together with the nitrogen atom, to which they are bonded may form a 5- or 6-membered ring; and $R_3$ is $C_1$-$C_{20}$alkyl;

(B2) hydroxyphenyl triazine derivatives corresponding to the formula

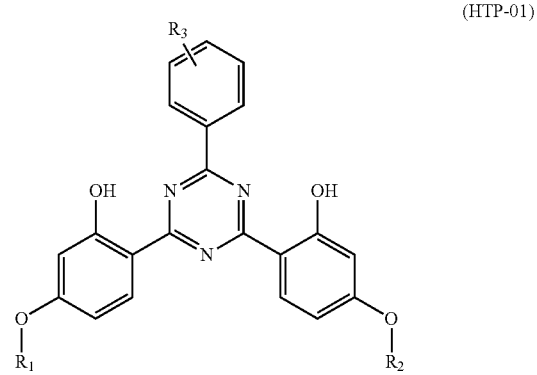

(HTP-01)

wherein $R_1$ and $R_2$ independently from each other are $C_1$-$C_{18}$alkyl; and $R_3$ is $C_1$-$C_{10}$alkoxy;

(B3) trianilino-s-triazine derivatives corresponding to the formula

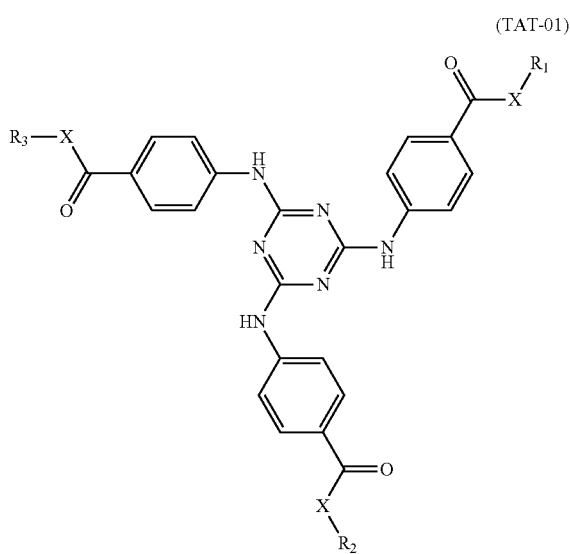

(TAT-01)

wherein

R₁, R₂ and R₃ independently from each other are $C_1$-$C_{20}$alkyl, $C_6$-$C_{10}$aryl or $C_6$-$C_{10}$eteroaryl;

X is O; or NR₄; and

R₄ is hydrogen; or C1-C20alkyl, aryl or heteroaryl;

and mixtures thereof.

2. The solubilizing agent according to claim 1, wherein; m1 and m2 have the same meaning.

3. The solubilizing agent according to claim 1, wherein the compounds of formula (1) are derived from lactic acid, glycolic acid, malic acid, tartaric acid or mixtures thereof.

4. The solubilizing agent according to claim 1, wherein the compound of formula (1) corresponds to formula (2)

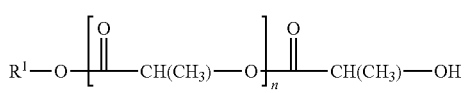

(2)

wherein

R¹ is hydrogen; or a linear or branched $C_1$-$C_{30}$ aliphatic hydrocarbon residue comprising 0, 1, 2 or 3 double bonds; and n is at least 0.1 on average.

5. The solubilizing agent according to claim 1, wherein n is a value from 0.1 to 100.

6. The solubilizing agent according to claim 1, wherein at least one of the radicals R¹, R⁴ and R⁵ in formula (1) is methyl; ethyl; n-propyl; isopropyl; n-butyl; isobutyl; sec.-butyl; tert.-butyl; n-pentyl; isoamyl; n-hexyl; 2-ethylhexyl; n-heptyl; n-octyl; n-nonyl, n-decyl, 2-propylheptyl, n-undecyl, n-dodecyl, n-tridecyl, n-tetradecyl, n-pentadecyl; n-hexadecyl; n-heptadecyl; n-octadecyl; n-nonadecyl; arachinyl; behenyl; lignocerinyl; melissinyl; isotridecyl; isostearyl; oleyl; linoleyl; linolenyl or a combination of at least two of these radicals.

7. The solubilizing agent according to claim 1, wherein at least one of the radicals R¹, R⁴ and R⁵ is derived from a mixture of linear saturated $C_{12}$-$C_{14}$-alcohols.

8. The solubilizing agent according to claim 1, wherein the organic UV filters (B) are used in admixtures of at least two different UV filters selected from (B1), (B2) and (B3).

9. The solubilizing agent according to claim 1, wherein the organic UV filter (B) is a benzophenone derivative (B1).

10. The solubilizing agent according to claim 1, wherein the benzophenone derivatives (B1) correspond to the formula

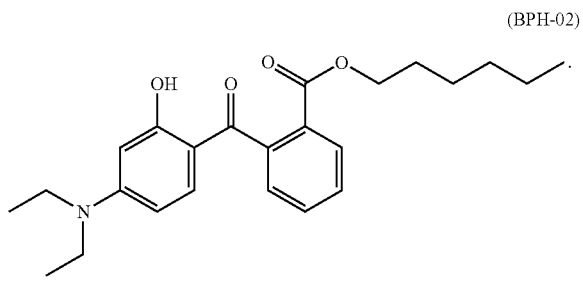 [SMILES: CCCCCCOC(=O)c1ccccc1C(=O)c1ccc(N(CC)CC)cc1O]

(BPH-02)

11. The solubilizing agent according to claim 1, wherein the organic UV filter (b) is a hydroxyphenyl triazine derivative (B2).

12. The solubilizing agent according to claim 1, wherein the hydroxyphenyl triazine derivatives (B2) correspond to formula

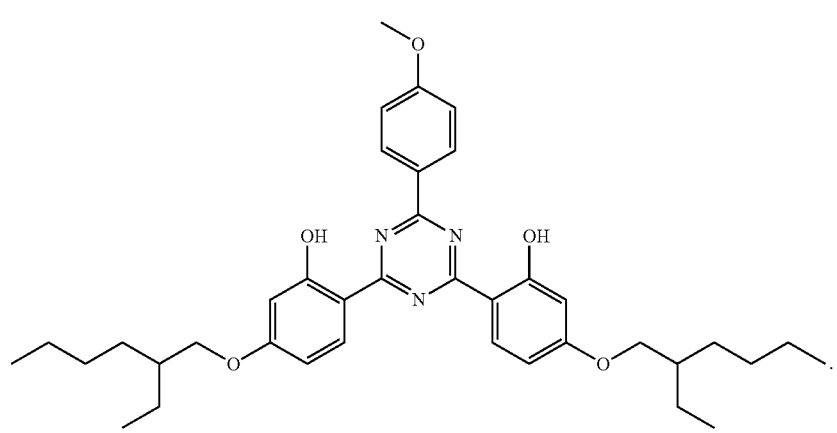

(HTP-02)

13. The solubilizing agent according to claim 1, wherein the hydroxyphenyl triazine derivatives (B2) correspond to formula

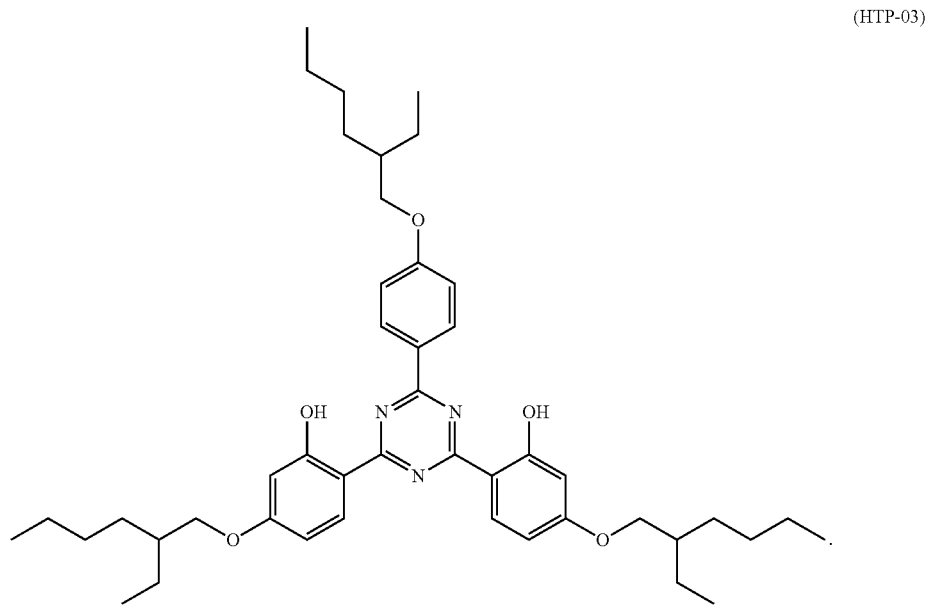 [SMILES: CCCCC(CC)COc1ccc(-c2nc(-c3ccc(OCC(CC)CCCC)cc3O)nc(-c3ccc(OCC(CC)CCCC)cc3O)n2)cc1]

(HTP-03)

14. The solubilizing agent according to claim 1, wherein the organic UV filter (B) is a trianilino-s-triazine derivative (B3).

15. The solubilizing agent according to claim 1, wherein the trianilino-s-triazine derivatives (B3) correspond to the formula

16. The solubilizing agent according to claim 1, wherein the organic UV filter is a mixture of a benzophenone derivative corresponding to the formula

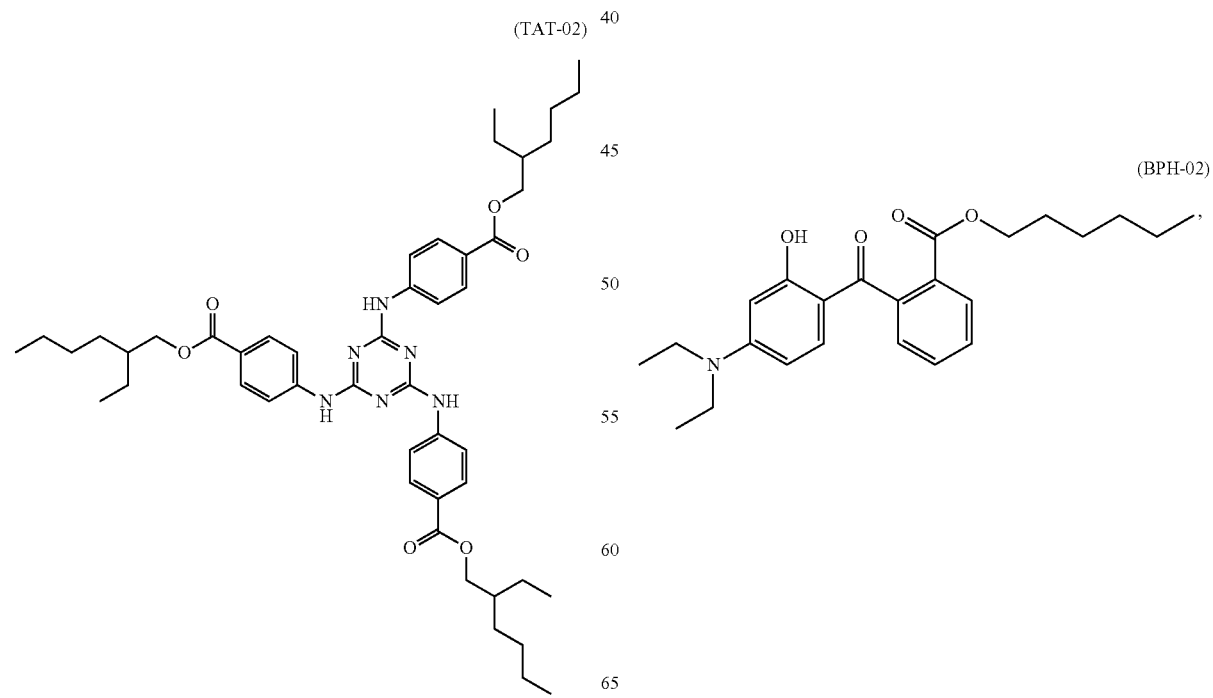

a hydroxyphenyl triazine derivative corresponding to formula

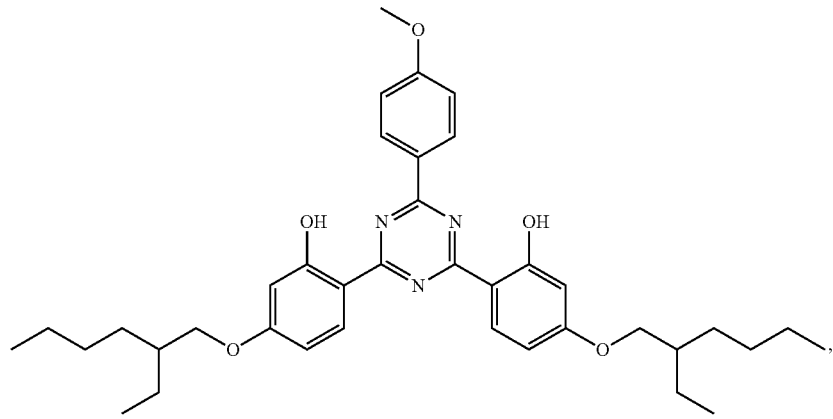
(HTP-02)
and a trianilino-s-triazine derivative corresponding to the formula
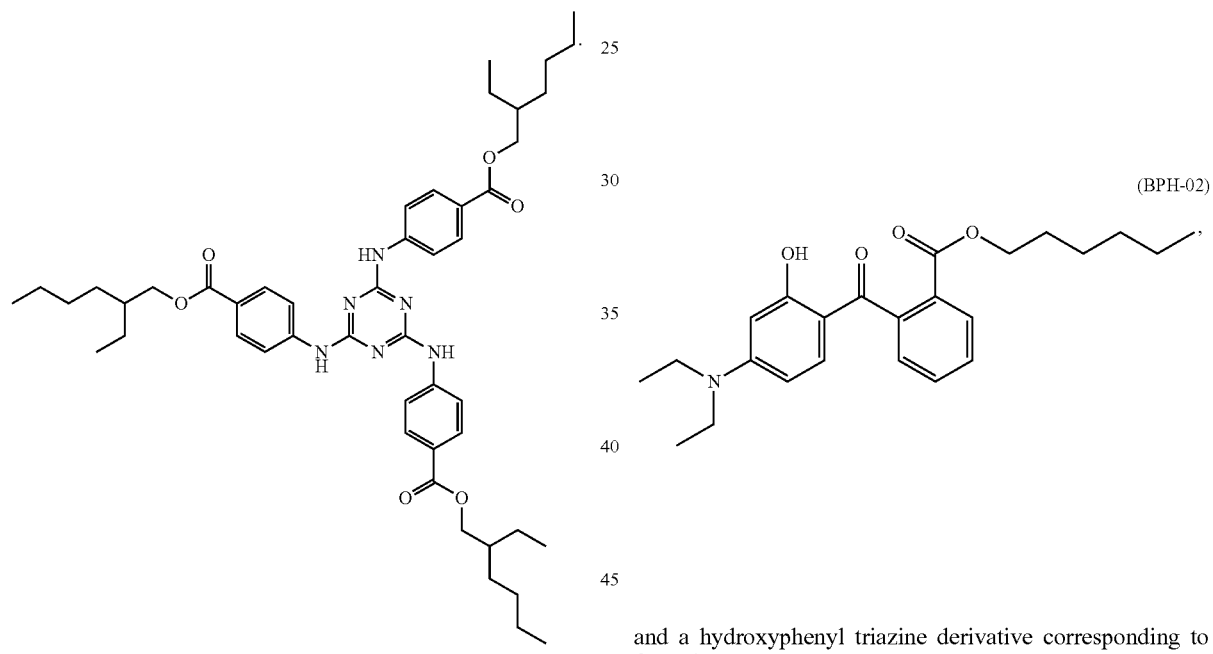
(TAT-02)
17. The solubilizing agent according to claim 1, wherein the organic UV filter is a mixture of
a benzophenone derivative corresponding to the formula
(BPH-02)
and a hydroxyphenyl triazine derivative corresponding to formula
(HTP-02)
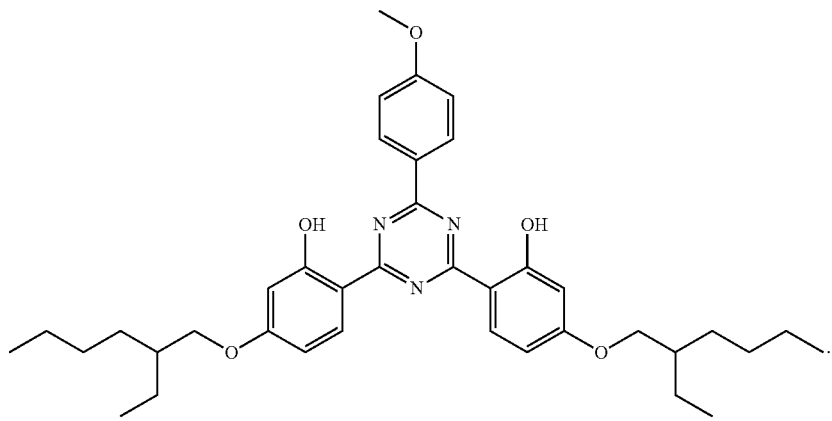

18. The solubilizing agent according to claim 1, wherein the organic UV filter is a mixture of
a benzophenone derivative corresponding to the formula (BPH-02)

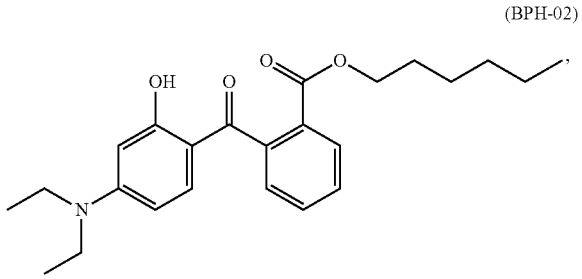 [SMILES: CCCCCCOC(=O)c1ccccc1C(=O)c1ccc(N(CC)CC)cc1O]

and a trianilino-s-triazine derivative corresponding to the formula (TAT-02)

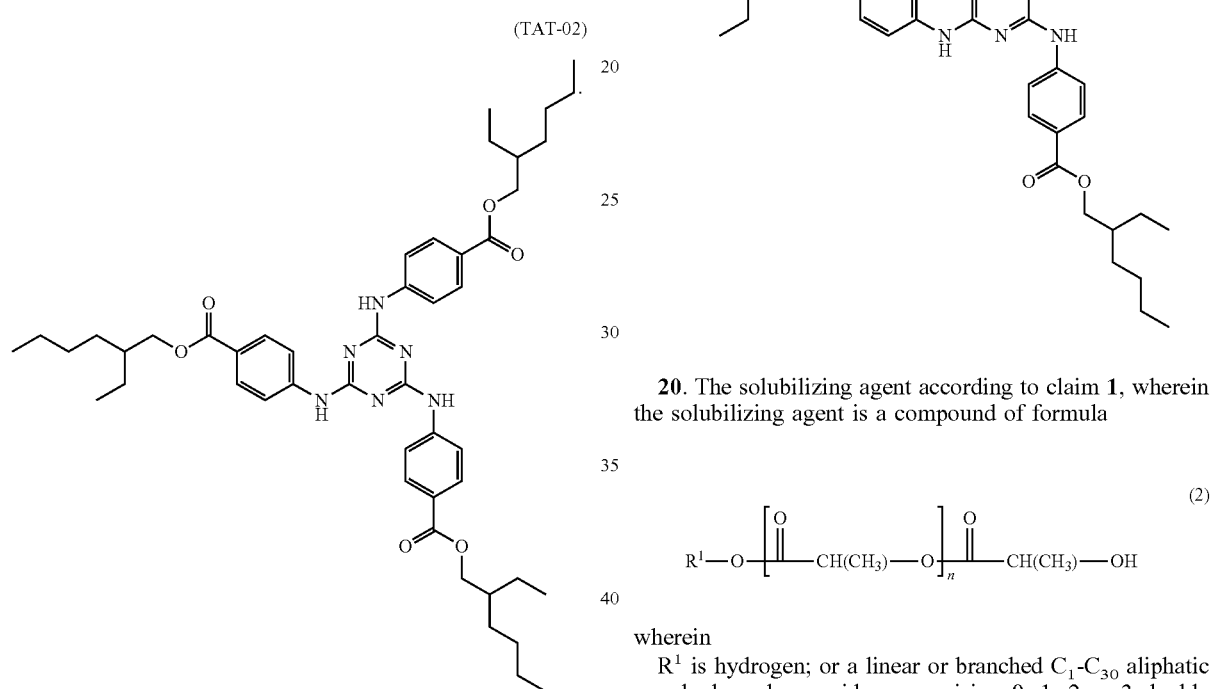

19. The solubilizing agent according to claim 1, wherein the organic UV filter is a mixture of
a hydroxyphenyl triazine derivative corresponding to formula (HTP-02)

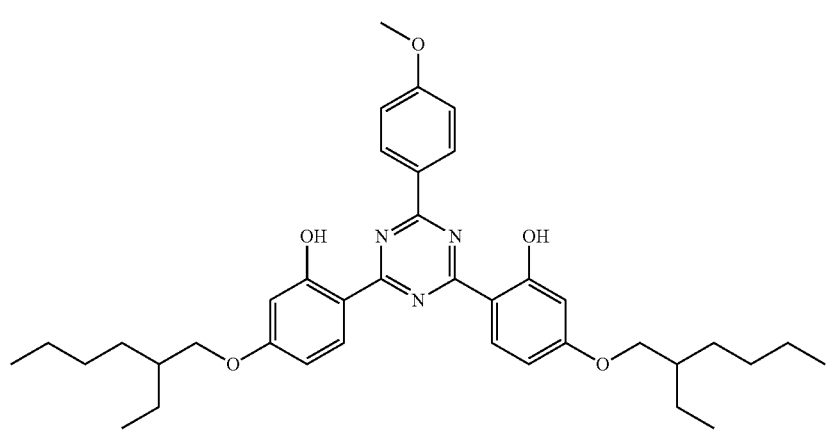

a trianilino-s-triazine derivative corresponding to the formula (TAT-02)

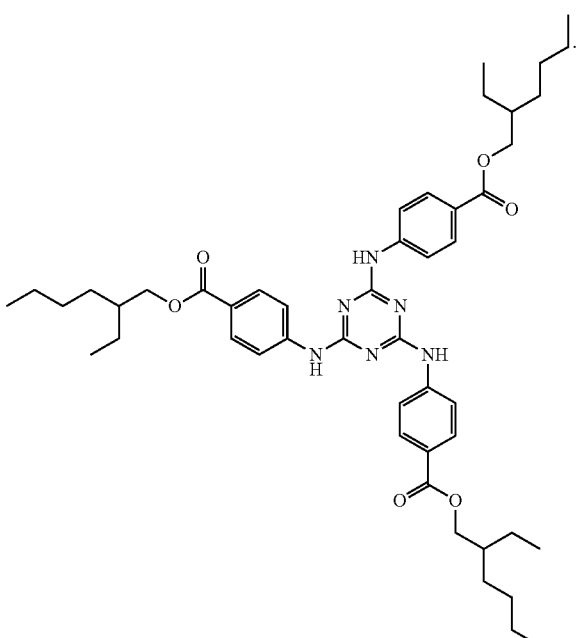

20. The solubilizing agent according to claim 1, wherein the solubilizing agent is a compound of formula (2)

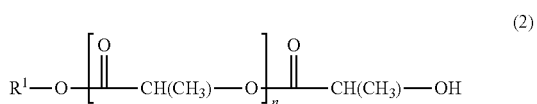

wherein
R$^1$ is hydrogen; or a linear or branched C$_1$-C$_{30}$ aliphatic hydrocarbon residue comprising 0, 1, 2 or 3 double bonds; and
n is at least 0.1 on average;
and the organic UV filter is selected from the group consisting of:

a benzophenone derivative corresponding to the formula (BPH-02)

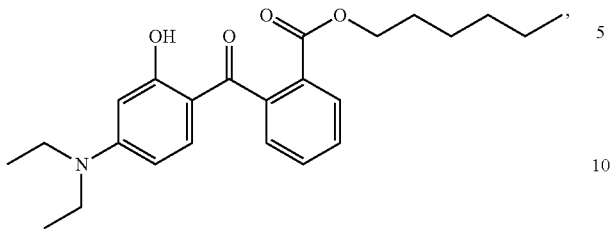

a hydroxyphenyl triazine derivative corresponding to formula

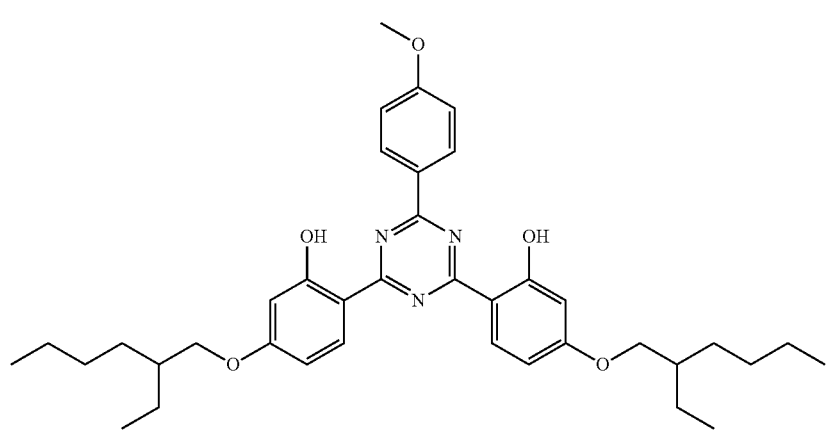

(HTP-02)

a trianilino-s-triazine derivative corresponding to the formula (TAT-02)

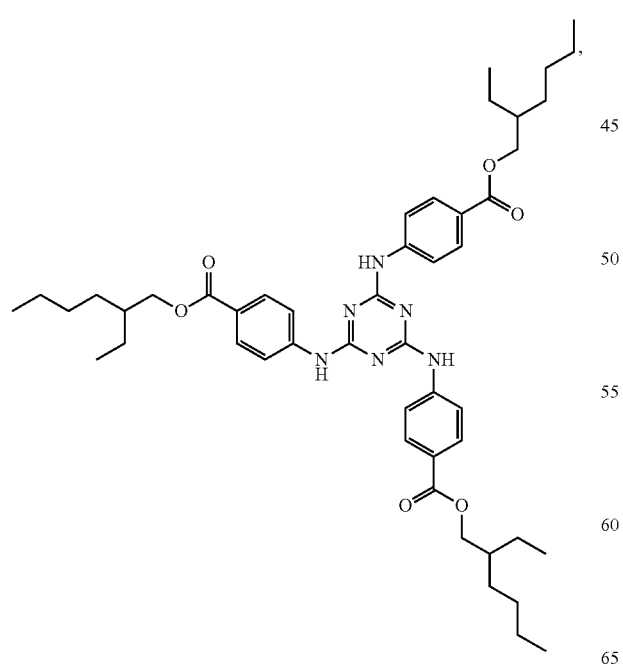

and mixtures thereof.

21. A cosmetic composition comprising (A) a compound of formula

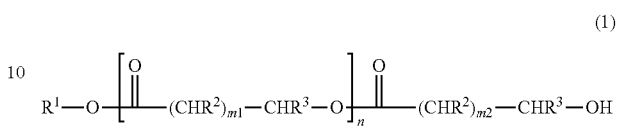

(1)

wherein

R$^1$ is hydrogen; or a linear or branched C$_1$-C$_{30}$ aliphatic hydrocarbon residue comprising 0, 1, 2 or 3 double bonds;

R$^2$ independently from each other are hydrogen; methyl; ethyl, —OH; —COOR$^4$; —CH$_2$—OH; or —CH$_2$—COOR$^4$;

R$^4$ is hydrogen; or a linear or branched C$_1$-C$_{30}$ aliphatic hydrocarbon residue comprising 0, 1, 2 or 3 double bonds;

R$^3$ independently from each other are hydrogen; methyl; ethyl; —OH; —COOR$^5$; —CH$_2$—OH; or —CH$_2$—COOR$^5$;

R$^5$ is hydrogen; or a linear or branched C$_1$-C$_{30}$ aliphatic hydrocarbon residue comprising 0, 1, 2 or 3 double bonds;

n is at least 0.1;

m1 and m2 independently from each other are 0 or 1;

with the proviso, that at least one of the radicals R1, R4 or R5 are a linear or branched C1-C30 aliphatic hydrocarbon residue comprising 0, 1, 2 or 3 double bonds; and (B) an organic UV filter selected from the group consisting of (B1) benzophenone derivatives corresponding to the formula (BPH-01)

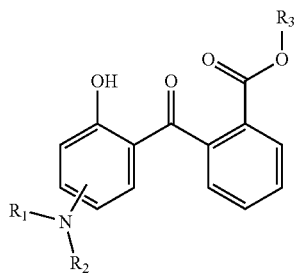

wherein
$R_1$ and $R_2$ independently from each other are hydrogen; $C_1$-$C_{20}$alkyl; $C_3$-$C_{10}$cycloalkyl; or $C_3$-$C_{10}$cycloalkenyl, wherein the radicals $R_1$ and $R_2$ together with the nitrogen atom, to which they are bonded may form a 5- or 6-membered ring; and
$R_3$ is $C_1$-$C_{20}$alkyl,
(B2) hydroxyphenyl triazine derivatives corresponding to the formula (HTP-01)

wherein
$R_1$ and $R_2$ independently from each other are $C_1$-$C_{18}$alkyl; and
$R_3$ is $C_1$-$C_{10}$alkoxy;
(B3) trianilino-s-triazine derivatives corresponding to the formula (TAT-01)

wherein
$R_1$, $R_2$ and $R_3$ independently from each other are $C_1$-$C_{20}$alkyl, $C_6$-$C_{10}$aryl or $C_6$-$C_{10}$eteroaryl;
X is O; or $NR_4$; and
$R_4$ is hydrogen; or C1-C20alkyl, aryl or heteroaryl,
and mixtures thereof.

22. The composition according to claim 21, wherein the solubilizing agent (A) corresponds to formula $$R^1-O-\left[\overset{O}{\underset{\|}{C}}-CH(CH_3)-O\right]_n\overset{O}{\underset{\|}{C}}-CH(CH_3)-OH \quad (2)$$

wherein
$R^1$ is hydrogen; or a linear or branched $C_1$-$C_{30}$ aliphatic hydrocarbon residue comprising 0, 1, 2 or 3 double bonds; and
n is at least 0.1 on average.

* * * * *